(12) United States Patent
Glauser et al.

(10) Patent No.: US 8,589,175 B2
(45) Date of Patent: Nov. 19, 2013

(54) OPTIMIZATION AND INDIVIDUALIZATION OF MEDICATION SELECTION AND DOSING

(75) Inventors: Tracy A. Glauser, Blue Ash, OH (US); Richard J. Wenstrup, Park City, UT (US); Alexander A. Vinks, Cincinnati, OH (US); John Pestian, Loveland, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 375 days.

(21) Appl. No.: 12/085,606

(22) PCT Filed: Nov. 28, 2006

(86) PCT No.: PCT/US2006/045631
§ 371 (c)(1),
(2), (4) Date: Jan. 13, 2009

(87) PCT Pub. No.: WO2007/064675
PCT Pub. Date: Jun. 7, 2007

(65) Prior Publication Data
US 2009/0171697 A1    Jul. 2, 2009

Related U.S. Application Data

(60) Provisional application No. 60/740,430, filed on Nov. 29, 2005, provisional application No. 60/783,118, filed on Mar. 16, 2006.

(51) Int. Cl.
*G06Q 50/00*    (2012.01)
(52) U.S. Cl.
USPC .............................................. 705/2; 600/300
(58) Field of Classification Search
USPC ................................. 705/2, 3; 600/300; 435/6
See application file for complete search history.

(56) References Cited

U.S. PATENT DOCUMENTS 5,648,482 A     7/1997   Meyer
5,833,599 A *  11/1998   Schrier et al. ................. 600/300

(Continued)

FOREIGN PATENT DOCUMENTS

EP        06 83 8538       5/2009
JP        2002024385 A     1/2002

(Continued)

OTHER PUBLICATIONS

Kirchheiner et al., CYP2D6 and CYP2C19 genotype-based dose recommendations for antidepressants: a first step towards subpopulation-specific dosages, Acta Psychiatr Scand 2001: 104: 173-192.*

(Continued)

*Primary Examiner* — Gerald J. O'Connor
*Assistant Examiner* — Jonathan K Ng
(74) *Attorney, Agent, or Firm* — Mintz Levin Cohn Ferris Glovsky and Popeo, P.C.; Ivor R. Elrifi; Muriel Liberto, Esq.

(57) ABSTRACT

The invention provides population models, methods, and algorithms for targeting a dosing regimen or compound selection to an individual patient. The methods and algorithms of the invention utilize population models that incorporate genotype information for genes encoding drug metabolizing enzymes for one or more compounds of interest. The methods allow integration of genotype information for one or more genes encoding a drug metabolizing enzyme, particularly a cytochrome P450 gene with patient data. The methods allow integration of genotype information and the effect of one or more compounds on one or more drug metabolizing enzymes. The methods allow iterative feedback of drug metabolizing data obtained from a patient into the process of generating a dosage regimen recommendation for a compound of interest for an individual patient.

6 Claims, 14 Drawing Sheets

(56) References Cited

U.S. PATENT DOCUMENTS

| | | | |
|---|---|---|---|
| 5,844,108 A | | 12/1998 | Meyer |
| 6,081,786 A * | | 6/2000 | Barry et al. ............... 705/3 |
| 6,183,963 B1 | | 2/2001 | Sinnett et al. |
| 6,188,988 B1 | | 2/2001 | Barry et al. |
| 6,251,587 B1 | | 6/2001 | Sevigny et al. |
| 6,251,608 B1 | | 6/2001 | Levy |
| 6,280,951 B1 | | 8/2001 | Heishi et al. |
| 6,291,175 B1 | | 9/2001 | Sevigny et al. |
| 6,297,014 B1 | | 10/2001 | Taylor et al. |
| 6,338,039 B1 | | 1/2002 | Lonski et al. |
| 6,368,797 B1 | | 4/2002 | Schappert |
| 6,399,310 B1 | | 6/2002 | Murphy, Jr. et al. |
| 6,432,648 B1 | | 8/2002 | Blumenfeld et al. |
| 6,434,542 B1 | | 8/2002 | Farmen et al. |
| 6,450,956 B1 * | | 9/2002 | Rappaport et al. ........ 600/300 |
| 6,472,421 B1 | | 10/2002 | Wolozin |
| 6,528,260 B1 | | 3/2003 | Blumenfeld et al. |
| 6,566,064 B1 | | 5/2003 | Shiraki et al. |
| 6,653,073 B1 | | 11/2003 | Comings et al. |
| 6,660,478 B1 | | 12/2003 | Kamataki |
| 6,675,166 B2 | | 1/2004 | Bova |
| 6,812,339 B1 | | 11/2004 | Venter et al. |
| 6,828,103 B2 | | 12/2004 | Herrington et al. |
| 6,861,217 B1 | | 3/2005 | Liggett |
| 6,912,492 B1 | | 6/2005 | Johnson et al. |
| 7,001,736 B1 | | 2/2006 | Poirier |
| 7,461,006 B2 * | | 12/2008 | Gogolak ..................... 705/2 |
| 7,546,285 B1 * | | 6/2009 | Baker, Jr. ...................... 1/1 |
| 7,809,585 B1 * | | 10/2010 | Ghouri ....................... 705/3 |
| 7,813,880 B2 * | | 10/2010 | Vaidya et al. ............ 702/19 |
| 2001/0034023 A1 | | 10/2001 | Stanton, Jr. et al. |
| 2002/0010552 A1 | | 1/2002 | Rienhoff et al. |
| 2002/0052761 A1 | | 5/2002 | Fey et al. |
| 2002/0076774 A1 * | | 6/2002 | Yan et al. .................. 435/183 |
| 2002/0082869 A1 | | 6/2002 | Anderson |
| 2002/0091664 A1 | | 7/2002 | Larder et al. |
| 2002/0091680 A1 | | 7/2002 | Hatzis et al. |
| 2002/0098498 A1 | | 7/2002 | Bader |
| 2002/0187483 A1 | | 12/2002 | Hoffman et al. |
| 2003/0046110 A1 | | 3/2003 | Gogolak |
| 2003/0046114 A1 | | 3/2003 | Davies et al. |
| 2003/0092034 A1 | | 5/2003 | Cooper et al. |
| 2003/0104453 A1 | | 6/2003 | Pickar et al. |
| 2003/0108938 A1 | | 6/2003 | Pickar et al. |
| 2003/0157110 A1 | | 8/2003 | An et al. |
| 2003/0170176 A1 | | 9/2003 | Leyland-Jones |
| 2003/0204320 A1 | | 10/2003 | Arouh et al. |
| 2003/0204415 A1 | | 10/2003 | Knowlton |
| 2004/0053257 A1 | | 3/2004 | Kelsoe, Jr. et al. |
| 2004/0082000 A1 | | 4/2004 | Stanton, Jr. |
| 2004/0133358 A1 | | 7/2004 | Bryant et al. |
| 2004/0193446 A1 * | | 9/2004 | Mayer et al. ................ 705/2 |
| 2004/0260666 A1 | | 12/2004 | Pestotnik et al. |
| 2005/0037366 A1 | | 2/2005 | Gut et al. |
| 2005/0060102 A1 | | 3/2005 | O'Reilly et al. |
| 2005/0084880 A1 | | 4/2005 | Duman et al. |
| 2005/0087880 A1 | | 4/2005 | Kujirai et al. |
| 2005/0260549 A1 * | | 11/2005 | Feierstein et al. ......... 434/236 |
| 2006/0166239 A1 * | | 7/2006 | Chen et al. ................. 435/6 |
| 2006/0280786 A1 * | | 12/2006 | Rabinow et al. ........... 424/450 |
| 2007/0003931 A1 * | | 1/2007 | Mrazek et al. ............. 435/6 |
| 2008/0311563 A1 | | 12/2008 | Mrazek et al. |

FOREIGN PATENT DOCUMENTS

| | | |
|---|---|---|
| JP | 2002197189 A | 7/2002 |
| JP | 2002245171 A | 8/2002 |
| WO | WO-0050639 A2 | 8/2000 |
| WO | WO-0212434 A2 | 2/2002 |
| WO | WO-03008637 A2 | 1/2003 |
| WO | WO 2004/074456 A3 | 9/2004 |
| WO | WO2005038049 * | 4/2005 |
| WO | WO 2005/109238 A2 | 11/2005 |
| WO | WO-2006075254 A2 | 7/2006 |
| WO | PCT/US06/45631 | 11/2006 |
| WO | PCT/US2006/045631 | 11/2006 |
| WO | WO-2008017038 A2 | 2/2008 |

OTHER PUBLICATIONS

Steimer W, Zöpf K, von Amelunxen S, Pfeiffer H, Bachofer J, Popp J, Messner B, Kissling W, Leucht S. Allele-specific change of concentration and functional gene dose for the prediction of steady-state serum concentrations of amitriptyline and nortriptyline in CYP2C19 and CYP2D6 extensive and intermediate metabolizers. Clin Chem. Sep. 2004;50(9):16.*

Kirchheiner J, Meineke I, Müller G, Roots I, Brockmöller J. Contributions of CYP2D6, CYP2C9 and CYP2C19 to the biotransformation of E- and Z-doxepin in healthy volunteers. Pharmacogenetics. Oct. 2002;12(7):571-80.*

Kirchheiner J, Nickchen K, Bauer M, Wong ML, Licinio J, Roots I, Brockmöller J. Pharmacogenetics of antidepressants and antipsychotics: the contribution of allelic variations to the phenotype of drug response. Mol Psychiatry. May 2004;9(5):442-73.*

Hung et al., Dosage recommendation of phenytoin for patients with epilepsy with different CYP2C9/CYP2C19 polymorphisms, Therapeutic Drug Monitoring. Nov. 2004; 26(5):534-40.*

Examiner's First Report regarding Australian Patent Application No. 2006320633 issued by Australian Patent Office on Oct. 1, 2010.

U.S. Appl. No. 11/498,976.

Children's Hospital Medical Center, Genetic Pharmacology Service for Children and Adults, Building a future of personalized medicine for children and adults (Brochure), USA [date unknown but prior to May 28, 2008].

Wilkinson, David S., The Role of Technology in the Clinical Laboratory of the Future, Clinical Laboratory Management Review, Sep./Oct. 1997, pp. 322-330, Medical College of Virginia, Virginia Commonwealth University, Richmond, Virginia, USA.

Hodgson, John, Shrinking DNA diagnostics to fill the markets of the future, Nature Biotechnology, Aug. 1998, pp. 725-727, vol. 16, Nature Publishing Group, USA.

Persidis, Aris, Biochips, Nature Biotechnology, Oct. 1998, pp. 981-983, vol. 16, Nature Publishing Group, USA.

Anderson, et al., A miniature integrated device for automated multistep genetic assays, Nucleic Acids Research, Apr. 15, 2000, pp. e60, i-vi, vol. 28, No. 12, Oxford University Press, England.

Wenner, et al., Genetically Designed Biosening Systems for High-Throughput Screening of Pharmaceuticals, Clinical Diagnostics, and Environmental Monitoring, Proceedings of SPIE vol. 4252, Jan. 24-25, 2001, pp. 59-70, San Jose, CA, USA.

Boren, et al., Commercialization of Evanescent Planar Waveguide (EPW TM) technology, Proceedings of SPIE vol. 4255, Jan. 21-22, 2001, pp. 63-66, San Jose, CA, USA.

Jenison, et al., Interference-based detection of nucleic acid targets on optically coated silicon, Nature Biotechnology, Jan. 2001, pp. 62-65, vol. 19, Nature Pub. Group, USA.

Lagally, et al., Fully integrated PCR-capillary electrophoresis microsystem for DNA analysis, Lab on a Chip, Dec. 2001, pp. 102-107, vol. 1, The Royal Society of Chemistry, United Kingdom.

Shimasaki, et al., Rapid Diagnostics: the detection of neuraminidase activity as a technology for high-specificty targets, Phil, Trans. The Royal Society Lond B Biol Sci, Dec. 29, 2001, pp. 1925-1931, vol. 356, No. 1416, ZymeTx, Inc., England.

Versalovic, et al., Molecular detection and genotyping of pathogens: more accurate and rapid answers, Trends in Microbiology, 2002, pp. S15-S21, vol. 10, No. 10, England.

Smekal, et al., Design, Fabrication and Testing of Thermal Components and their Integration into a Microfluidic Device, Inter. Society Conference on Thermal Pheonomena, 2002, pp. 1039-1045, San Diego, CA, USA.

Huang, et al., MEMS-based sample preparation for molecular diagnostics, Anal Bioanal Chem, pp. 49-65, vol. 372, Nanogen, Inc., San Diego, CA, USA.

Tong, et al., Moving to nucleic acid-based detection of genital *Chlamydia trachomatis*, Expert Rev Mol Diagn, May 2002, pp. 257-266, King's College London, UK.

(56) References Cited

OTHER PUBLICATIONS

Fortina, et al., Molecular diagnostics: hurdles for clinical implementation, TRENDS in Molecular Medicine, Jun. 2002, vol. 8, No. 6, The Children's Hospital of Philadelphia, Philadelphia, PA, USA.

Thomas, et al., BioMEMS using electrophoresis for the analysis of genetic mutations, Expert Rev Mol Diagn, Sep. 2002, pp. 429-447, National Institute of Standards and Technology, Gaithersburg, MD USA.

Muller, et al., Improvement of molecular monitoring of residual disease in leukemias by bedside RNA stabilization, Leukemia, Dec. 2002, pp. 2395-2399, vol. 16, No. 12, Universitat Heidelberg, Mannheim, Germany.

Sosnowski, et al., Active microelectronic array system for DNA hybridization, genotyping and pharmacogenomic applications, Dec. 2002, pp. 181-192. vol. 12, Nanogen, Inc., USA.

Jain, KK, Nanodiagnostics: application of nanotechnology in molecular diagnostics, Expert Rev Mol Diagn, Mar. 2003, pp. 153-161, Jain PharmaBiotech, Basel, Switzerland.

Lin, et al., A Prediction Model for the Drug Efficacy of Inteferon in CHC Patients Based on SNPs, IEEE Computational Systems Bioinformatics Conf., 2004, Vita Genomics, Taiwan.

Tyre, et al., Finding What Works, Newsweek, Apr. 25, 2005, pp. 54-56, USA.

Gianneschi, et al., Design of Molecular Logic Devices Based on a Programmable DNA-Regulated Semi-Synthetic Enzyme, The Scripps Research Institute, 2007, p. 1-5, Lo Jolla, CA.

Saghatelian, et al., DNA Detection and Signal Amplification via an Engineered Allosteric Enzyme, J. Am. Chem. Soc., 2003, pp. 344-345, vol. 125, No. 2, La Jolla, CA, USA.

Gianneschi, et al., Design of Molecular Logic Devices Based on a Programmable DNA-Regulated Semisynthetic Enzyme, Angew. Chem. Int. Ed., 2007, pp. 3955-3958, vol. 46, Wiley-VCH Verlag GmbH & Co. KGaA, Weinheim, Germany.

Rutherglen, et al., RF resistance and inductance of massively parallel single walled carbon nanotubes: Direct, broadband measurements and near perfect 50 Ohm impedance matching, Applied Physics Letters, Aug. 28, 2008, 93, 083119(3), American Institute of Physics, USA.

Woolard, et al., Nanoscale Imaging Techology for THz-Frequency Transmission Microscopy, International Journal of High Electronics and Systems, 2008, pp. 205-222, vol. 18, No. 1, World Scientific Publishing Company, USA.

Zhou, et al., Wafer Scale Synthesis of Dense Aligned Arrays of Single-Walled Carbon Nanotubes, Nano Research, Jun. 7, 2008, pp. 158-165, vol. 1, No. 2, Tsinghua Press and Springer-Verlag, Germany.

Rutherglen, et al., Carbon Nanotube Radio, Nano Letters, 2007, pp. 3296-3299, vol. 7. No. 11, American Chemical Society, USA.

Burke, et al., Single-Walled Carbon Nanotubes: Applications in High Frequency Electronics, International Journal of High Speed Electronics and Systems, 2006, pp. 977-999, vol. 16, No. 4, World Scientific Publishing Company, USA.

Kang, et al., Resonant frequency response of plasma wave detectors, Applied Physics Letters, 2006, 89, 213512(3), American Inst. of Physics, USA.

Burke, et al., Quantitative Theory of Nanowire and Nanotube Antenna Performance, IEEE Transactions on Nanotechnology. Jul. 2006, pp. 314-334, vol. 5, No. 4, Institute of Electrical and Electronics Engineers, Inc, Piscataway, New Jersey, USA.

Yu, et al., Microwave nanotube transistor operation at high bias, Applied Physics Letters, 2006, 88, 23315(3), American Institute of Physics, USA.

Kang, et al., AC ballistic transport in a two-dimensional electron gas measured in GaAs/AlGaAs heterostructures, Physical Review, 2005, 72, 165312(5), The American Physical Society, USA.

Yu, et al., Microwave Transport in Metallic Single-Walled Carbon Nanotubes, Nano Letters, 2005, pp. 1403-1406, vol. 5, No. 7, American Chemical Society, USA.

Li, et al., Silicon nitride gate dielectric for top-gated carbon nanotube field effect transistors, Journal of Vacuum Science & Technology B: Microelectronics and Nanometer Structures, 2004, vol. 22, No. 6, pp. 3112-3114, American Vacuum Society, USA, also published in Virtual Journal of Nanoscience and Technology, 2004, vol. 10, No. 26.

Li, et al., Electrical Properties of 0.4 cm Long Single-Walled Carbon Nanotubes, Nano Letters, 2004, pp. 2003-2007 plus 3 page supplement, vol. 4, No. 10, American Chemical Society, USA.

Zheng, et al., Manipulating Nanoparticals in Solution with Electrically Contacted Nanotubes Using Dielectrophoresis, Langmuir, 2004, pp. 8612-8619, vol. 20, No. 20, American Chemical Society, USA.

Yu, et al., Synthesis of Aligned Arrays of Millimeter Long, Straight Single-Walled Carbon Nanotubes. Chemistry of Materials, 2004, pp. 3414-3416 plus 3 page supplement, vol. 16, No. 18, American Chemical Society, USA.

Burke, Peter J, AC performance of nanoeletronics: towards a ballistic THz nanotube transistor, Solid-State Electronics, 2004, pp. 1981-1986, vol. 48, No. 10, Elsevier, Amsterdam, The Netherlands.

Kang, et al., Ballistic transport at GHz frequencies in ungated HEMT structures, Solid-State Electronics, 2004, pp. 2013-2017, vol. 48, No. 10, Elsevier, Amsterdam, The Netherlands.

Zheng, et al., Electronic manipulation of DNA, proteins, and nanoparticles for potential circuit assembly, Biosensors & Bioelectronics, 2004, pp. 606-619, vol. 20, No. 3, Elsevier, Amsterdam, The Netherlands.

Li, et al., Carbon Nanotube Transistor Operation at 2.6 GHz, Nano Letters, 2004, pp. 753-756, vol. 4, No. 5, American Chemical Society, USA.

Burke Peter J., An RF Circuit Model for Carbon Nanotubes, IEEE Transactions on Nanotechnology, 2003, pp. 555-558, vol. 2, vol. 1, Institute of Electrical and Electronics Engineers, Inc., Piscataway, New Jersey, USA, corrections 2004, p. 331, vol. 3, No. 2.

Burke Peter J., Luttinger Liquid Theory as a Model of the Gigahertz Electrical Properties of Carbon Nanotubes, IEEE Transactions on Nanotechnology, 2002, pp. 129-144, vol. 1, No. 3, Institute of Electrical and Electronics Engineers, Inc., Piscataway, New Jersey, USA, corrections 2004, p. 331, vol. 3, No. 2.

Peralta, et al., THz Detection by Resonant 2-D Plasmons in Field Effect Devices, International Journal of High Speed Electronics and Systems, 2002, pp. 925-937, vol. 12, No. 3, World Scientific Publishing Company, USA.

Peralta, et al., Terahertz photoconductivity and plasmon modes in double-quantum-well field-effect transistors, Applied Physics Letters, 2002, pp. 1627-1629, vol. 81, No. 9, American Institute of Physics, USA.

Burke, et al., Effect of Nyquist noise on the Nyquist dephasing rate in two-dimensional electron systems, Physical Review B, 2002, vol. 65, 201310(4), The American Physical Society, USA, also in Virtual Joural of Nanoscale Science & Technology, Jun. 3, 2002.

Burke, et al., An all-cryogenic THz transmission spectrometer, Review of Scientific Instruments, 2002, pp. 130-135, vol. 73, No. 1, American Institute of Physics, USA.

Burke, et al., High frequency conductivity of the high-mobility two-dimensional electron gas, Applied Physics Letters, 2000, pp. 745-747, vol. 76, No. 6, American Insitute of Physics, USA.

Burke, et al., Mixing and noise in diffusion and phonon cooled superconducting hot-electron bolometers, Journal of Applied Physics, 1999, pp. 1644-1653, vol. 85, No. 3, American Institute of Physics, USA.

Burke, et al., Spectrum of thermal fluctuation noise in diffusion and phonon cooled hot-electron mixers, Applied Physics Letters, 1998, pp. 1516-1518, vol. 72, No. 12, American Institute of Physics, USA.

Schoelkopf, et al., Noise bandwidth of diffusion-cooled hot-electron bolometers, IEEE Transactions on Applied Superconductivity, 1997, pp. 3576-3579, vol. 7, No. 2, Institute of Electrical and Electronics Engineers, Inc., Piscataway, New Jersey, USA.

Schoelkopf, et al., Frequency Dependence of Shot Noise in a Diffusive Mesoscopic Conductor, Physical Review Letters, 1997, pp. 3370-3373, vol. 78, No. 17, The American Physical Society, USA.

Burke, et al., Length scaling of bandwidth and noise in hot-electron superconducting mixers, Applied Physics Letters, 1996, pp. 3344-3346, vol. 68, No. 23, American Institute of Physics, USA.

(56) References Cited

OTHER PUBLICATIONS

Skalare, et al., Large bandwidth and low noise in a diffusion-cooled hot-electron bolometer mixer, Applied Physics Letters, 1996, pp. 1558-1560, vol. 68, No. 11, American Institute of Physics, USA.
Skalare, et al., A Heterodyne Receiver at 533 GHz using a Diffusion-Cooled Superconducting Hot Electron Bolometer Mixer, IEEE Transactions on Applied Superconductivity, 1995, pp. 2236-2239, vol. 5, No. 2, Institute of Electrical and Electronics Engineers, Inc., Piscataway, New Jersey, USA.
Burke, P.J., Nanodielectrophoresis: Electronic Nanotweezers, Encyclopedia of Nanoscience and Nanotechnology, 2003, pp. 623-641, vol. 6, American Scientific Publishers, USA.
Peralta, et al., THz Detection on Resonant 2-D Plasmons in Field Effect Devices, Frontiers in Electronics, 2002, pp. 333-345, World Scientific, River Edge, New Jersey, USA.
Zheng, Lifeng, Nanotube Interactions with Nanoparticles and Peptides—Ph.D. Dissertaion, 2008, University of California, Irvine—unpublished.
Kang, Sungmu, Devices Using Ballistic Transport of Two Dimensional Electron Gas in delta doped GaAs High Electron Mobility Transistor Structures—Ph.D. Dissertation, 2006, University of California, Irvine—unpublished.
Li, Shengdong, Carbon Nanotube High Frequency Devices—Masters Thesis, 2004, University of California, Irvine—unpublished.
Burke, et al., Interlayer Plasmons, 1998, unpublished.
Burke, Peter John, High Frequency Electron Dynamics in Thin Film Superconductors and Applications to Fast, Sensitive THz Detectors—Ph.D. Dissertaion, 1997, Yale University—unpublished.
Zhou, et al., Nanotube arrays synthesis for microwave applications, Proc. IEEE Internation Symposium on Antennas & Propagation, 2008, Institute of Electrical and Electronics Engineers, Inc., Piscataway, New Jersey, USA—Abstract.
Kang, et al., RF Circuit Model of a Quantum Point Contact, Technical Program & Abstract Digest for the 2008 International Symposium on Spectrum on Spectral Sensing Research, 2008—Abstract.
Burke, et al., THz Spectral Sensing with Nanotechnology: An Overview, Technical Program & Abstract Digest for the 2008 International Symposium on Spectral Sensing Research, 2008—Abstract.
Rutherglen, et al., Carbon Nanotube Radio: Demonstration of a CNT Based Am Demodulator, Technical Program & Abstract Digest for 2007 Nanoelectronic Devices for Defense & Security (Nano-DDS) Conference, 2007—Abstract.
Burke, et al., A Possible Architecture for Wirelessly Integrated RF Nanosystems, Technical Program & Abstract Digest for 2007 Nanoelectronic Devices for Defense & Security (Nano-DDS) Conference, 2007—Abstract.
Burke, et al., Carbon Nanotube Antennas, Nanomodeling II, 2006, vol. 6328, 632806-1, Proc. SPIE International Society of Optical Engineers, Bellingham, WA, USA.
Yu, et al., Scaling of the microwave and dc conductance of metallic single-walled carbon nanotubes, Nanostructure Integration for Manufactureable Devices, Circuits and Systems: Interfaces, Interconnects, and Nanosystems, 2005, vol. 6003, 60030Q, Proc. SPIE International Society of Optical Engineers, Bellingham, WA, USA.
Kang, et al., Design, fabrication, and impedance of plasma wave detectors, Chemical and Biological Standoff Detection III, 2005, vol. 5995, 59950M, Proc. SPIE International Society of Optical Engineers, Bellingham, WA, USA.
Burke, et al., Carbon Nanotube Antennas, Proc. of 9th International Conference on Eletromagnetics in Advanced Applications, 2005, 937.
Burke, et al., Carbon Nanotubes for RF and Microwaves, Proc. of European Microwave Week, 2005, pp. 1-5, invited plenary talk, 13th GAAS Symposium, Paris, France.
Burke, et al., Nanotube Technology for Microwave Applications, Proc. of IEEE MTT International Microwave Symposium 2005, 2005, invited.
Yu, et al., Using ultra-long nanotubes to make identical CNT FETs, NSTI-Nanotech 2005 Proceedings, 2005, pp. 123-125, vol. 3, Nano Science and Technology Institute, Cambrige, MA, USA.
Yu, et al., Aligned Array FETs as a Route Towards THz Nanotube Transistors, Terahertz for Military and Security Applications III, 2005, pp. 246-253, vol. 5790, Proc. of SPIE International Society of Optical Engineers, Bellingham, WA, USA.
Burke, Peter J., Carbon Nanotube Devices for GHz to THz Applications, Nanosensincy Materials and Devices, 2004, pp. 52-61, vol. 5593, Proc. of SPIE International Society of Optical Engineers, Bellingham, WA, USA, invited paper.
Zheng, et al., Self-Assembled Gold Nanowires from Nanoparticles: An Electronic Route Towards DNA Nanosensors, Nanoengineering: Fabrication, Properties, Optics, and Devices, 2004, pp. 117-124, vol. 5515, Proc. of SPIE International Society of Optical Engineers, Bellingham, WA, USA.
Yen, et al., GHz Electrical Properties of Carbon Nanotubes on Silicon Dioxide Micro Bridges, Proc. of Nanotech2004, 2004, pp. 1-6.
Lee, et al., Electrochemiluminescence as a tool for microscopy at the nanoscale, Nanobiophotonics and Biomedical Applications, 2004, pp. 13-20, vol. 5331, Proc. of SPIE International Society of Optical Engineers, Bellingham, WA, USA.
Zheng, et al., Eletronic manipulation of DNA and proteins for potential nano-bio circuit assembly, Nanobiophotonics and Biomedical Applications, 2004, pp. 126-135, vol. 5331, Proc. of SPIE International Society of Optical Engineers, Bellingham, WA, USA.
Burke, Peter J., Carbon Nanotube Devices for GHz to THz Applications, 2003, pp. 314-315, Proc. of the 2003 International Semiconductor Device Research.
Kang, et al., Crossover from diffusive to ballistic transport as a function of frequency in a two dimensional electron gas, 2003, pp. 198-199, Proc. of the 2003 International Semiconductor Device Research Symposium—Student Paper.
Zheng, et al., Towards Single Molecule Manipulication with Dielectrophoresis Using Nanoelectrodes, Proc. of the 3rd IEEE Conference on Nanotechnology, 2003, pp. 437-440, vol. 1,Institute of Electrical and Electronics Engineers, Inc., Piscataway, NJ, USA.
Li, et al., Carbon Nanotube Growth for GHz Devices, Proceedings of the 3rd IEEE Conference on Nanotechnology, 2002, pp. 256-259, vol. 1, Institute of Electrical and Electronics Engineers, Inc., Piscataway, NJ, USA.
Burke, et al., An RF Circuit Model for Carbon Nanotubes, Proceedings of the IEEE Conference on Nanotechnology 2002, 2002, pp. 393-396, Institutes of Electrical and Electronics Engineers, Inc., Piscataway, NJ, USA.
Peralta, et al., In-Plane magneto-plasmons in grating gated double quantum well field effect transistors, Proceedings of the 26th International Conference on the Physics of Semiconductors, 2002, pp. 1-8, Edinburgh, England.
Kang, et al., High Mobility 2DEGs, Poster at First Annual Research Review, 2002, The Henry Samueli School of Engineering, Irvine, CA, USA.
Liu, et al., Nanobiotechnology: Electronic Control of Biochemical Reactions at the Nanoscale, Poster at First Annual Research Review, 2002, The Henry Samueli School of Engineering, Irvine CA, USA.
Peralta, et al., Resonant Terahertz Photoconductance of Grating Gated Double Quantum Well Field Effect Transistors, Proc. of FAR-IR, SUB-MM & MM Detector Technology Workshop, 2002, NASA/CP-211408.
Karasik, et al., Low-noise and wideband hot-electron superconductive mixer for THz frequencies, 4th International Conference on Millimeter and Submillimeter Waves and Applications, 1998, pp. 170-179, vol. 3465, SPIE International Society of Optical Engineering, Bellingham, WA, USA.
Burke, et al., Noise performance of diffusion cooled-hot-electron bolometers: theory v. experiment, Ninth International Symposium on Space Terahertz Technology, 1998, pp. 17-33, Pasadena, CA, USA.
Wolinsky, Steven M., www.medicine.northwestern.edu/scripts/bio.pl?pid=795, Chicago, IL, USA.
Schoelkopf, et al., Spectrum of output noise in diffusion and phonon cooled hot electron superconducting mixers, Seventh International Symposium on Space Terehertz Technology, 1996, pp. 318-331, University of Virginia, VA, USA.
Skalare, et al., Noise Temperature and if Bandwidth of a 530 GHz Diffusion-Colled Hot-Electron Bolometer Mixer, Sixth International

(56) References Cited

OTHER PUBLICATIONS

Symposium on Space Terehertz Technology, 1995, pp. 262-267, California Institute of Technology, Pasadena, CA, USA.
Skalare, et al., A Superconducting Hot Electron Bolometer Mixer for 530 GHz, Fifth International Symposium on Space Terahertz Technology, 1994, pp. 157-168, University of Michigan, Ann Arbor, MI, USA.
Prober, et al., Superconducting Terahertz Mixer Using a transition Edge Microbolometer, Proceedings of the 1993 International Semiconductor Device Research Symposium, 1993, University of Virginia, VA, USA.
Wilkinson, David S., The Role of Technology in the Clinical Laboratory of the Future, Clinical Laboratory Management Review, 1997, pp. 322-330, September/October Volume, Clinical Laboratory Management Association, Inc.
Miners et al. "Cytochrome P4502C9: An Enzyme of Major Importance in Human Drug Metabolism." *Br. J. Clin. Pharmacol.* 45.6(1998):525-538.
Brockmöller et al. "Pharmacogenetic Diagnostics of Cytochrome P450 Polymorphisms in Clinical Drug Development and in Drug Treatment." *Pharmacogenomics.* 1.2(2000):125-151.
Ereshefsky et al. "Review of the Pharmacokinetics, Pharmacogenetics, and Drug Interaction Potential of Antidepressants: Focus on Venlafaxine." *Depress. Anxiety.* 12.S1(2000):30-44.
Griese et al. "Assessment of the Predictive Power of Genotypes for the in-vivo Catalytic Function of CYP2D6 in a German Population." *Pharmacogenetics.* 8.1(1998):15-26.
Ibeanu et al. "A Novel Transversion in the Intron 5 Donor Splice Junction of *CYP2C19* and a Sequence Polymorphism in Exon 3 Contribute to the Poor Metabolizer Phenotype for the Anticonvulsant Drug S-Mephenytoin." *J. Pharmacol. Exp. Ther.* 290.2(1999):635-640.
Ingelman-Sundberg et al. "Polymorphic Human Cytochrome P450 Enzymes: An Opportunity for Individualized Drug Treatment." *Trends Pharmacol. Sci.* 20.8(1999):342-349.
McElroy et al. "CYP2D6 Genotyping as an Alternative to Phenotyping for Determination of Metabolic Status in a Clinical Trial Setting." *AAPS Pharmsci.* 2.4(2000):1-11.
Meisel et al. "How to Manage Individualized Drug Therapy: Application of Pharmacogenetic Knowledge of Drug Metabolism and Transport." *Clin. Chem. Lab. Med.* 38.9(2000):869-876.
Sachse et al. "Functional Significance of a C→A Polymorphism in Intron I of the Cytochrome P450 *CYP1A2* Gene Tested With Caffeine." *Br. J. Clin. Pharmacol.* 47(1999):445-449.
Sallee et al. "Fluoxetine-Related Death in a Child With Cytochrome P-450 2D6 Genetic Deficiency." *J. Child Adol. Psychopharmacol.* 10.1(2000):27-34.
Wong et al. "Pharmacogenetics: The Molecular Genetics of *CYP2D6* Dependent Drug Metabolism." *Ann. Acad. Med. Singapore.* 29.3(2000):401-406.
Arranz et al. "Pharmacogenetics for the Individualization of Psychiatric Treatment." *Am. J. Pharmacogenomics.* 1.1(2001):3-10.
Bishop et al. "Neuropsychiatric Pharmacogenetics: Moving Toward a Comprehensive Understanding of Predicting Risks and Response." *Pharmacogenomics.* 5.5(2004):463-477.
Bondy et al. "Pharmacogenetics and Psychopharmacology." *Curr. Opin. Pharmacol.* 4.1(2004):72-78.
Catalano et al. "Functionally Gene-Linked Polymorphic Regions and Genetically Controlled Neurotransmitters Metabolism." *Eur. Neuropsychopharmacol.* 11(2001):431-439.
Chou et al. "Comparison of Two CYP2D6 Genotyping Methods and Assessment of Genotype-Phenotype Relationships." *Clin. Chem.* 49.4(2003):542-551.
Coutts et al. "Polymorphic Cytochromes P450 and Drugs Used in Psychiatry." *Cell. Mol. Neurobiol.* 19.3(1999):325-354.
Dalma-Weiszhausz et al. "Single Nucleotide Polymorphisms and Their Characterization with Oligonucleotide Microarrays." *Psychiatric Genetics.* 12.2(2002):97-107.
DeVane. "Pharmacogenetics and Drug Metabolism of Newer Antidepressant Agents." *J. Clin. Psychiatry.* 55(1994):38-47.
Drmanac et al. "DNA Sequence Determination by Hybridization: A Strategy for Efficient Large-Scale Sequencing." *Science.* 260(1993):1649-1652.
Evans et al. "Pharmacogenomics: Translating Functional Genomics into Rational Therapeutics." *Science.* 286.5439(1999):487-491.
Hewett et al. "PharmGKB: The Pharmacogenetics Knowledge Base." *Nucleic Acids Res.* 30.1(2002):163-165.
Jain. "Application of Biochip and Microarray Systems in Pharmacogenomics." *Pharmacogenomics.* 1.3(2000):289-307.
Johnson et al. "Pharmacogenomics: A Scientific Revolution in Pharmaceutical Sciences and Pharmacy Practice." *Am. J. Pharma. Educ.* 66(2002):12S-15S.
Kawanishi et al. "Pharmacogenetics and Schizophrenia." *Eur. J. Pharmacol.* 410.2-3(2000):227-241.
Kerwin et al. "Genetic Strategies for the Personalization of Antipsychotic Treatment." *Exp. Rev. Mol. Diag.* 1.3(2001):275-280.
Kim et al. "Serotonin Transporter Gene Polymorphism and Antidepressant Response." *NeuroReport.* 11(2000):215-219.
Kirchheiner et al. "Pharmacogenetics-Based Therapeutic Recommendations—Ready for Clinical Practice?" *Nat. Rev. Drug Discov.* 4.8(2005):639-647.
Klein et al. "Integrating Genotype and Phenotype Information: An Overview of the PharmGKB Project." *Pharmacogenomics J.* 1(2001):167-170.
Lachman et al. "Human Catechol-*O*-methyltransferase Pharmacogenetics: Description of a Functional Polymorphism and its Potential Application to Neuropsychiatric Disorders." *Pharmacogenetics.* 6(1996):243-250.
Letter from third party dated Jun. 12, 2013.
Luo et al. "Identification of *CYP2D6* Impaired Functional Alleles in Mexican Americans." *Eur. J. Clin. Pharmacol.* 61(2005):797-802.
McAlpine et al. "Cytochrome P450 *2D6* Genotype Variation and Venlafaxine Dosage." *Mayo Clin. Proc.* 82.9(2007):1065-1068.
Minov et al. "Serotonin-2A-Receptor and -Transporter Polymorphisms: Lack of Association in Patients with Major Depression." *Neurosci. Lett.* 303(2001):119-122.
Mitchell. "Therapeutic Drug Monitoring of Psychotropic Medications." *Brit. J. Clin. Pharmacol.* 49.4(2000):303-312.
Raimundo et al. "A Novel Intronic Mutation, 2988G>A, with High Predictivity for Impaired Function of Cytochrome P450 2D6 in White Subjects." *Clin. Pharmacol. Ther.* 76.2(2004):128-138.
Rasmussen et al. "CYP2D6 Gene Test in Psychiatric Patients and Healthy Volunteers." *Scand. J. Clin. Lab. Invest.* 66(2006):129-136.
Seretti et al. "Influence of Tryptophan Hydroxylase and Serotonin Transporter Genes on Fluvoxamine and Antidepressant Activity." *Mol. Psych.* 6(2001):586-592.
Serretti et al. "Pharmacogenetics in Affective Disorders." *Eur. J. Pharmacol.* 438.3(2002):117-128.
Steimer et al. "Pharmacogenetic Screening and Therapeutic Drugs." *Clinica Chimica Acta.* 315.1-2(2002):137-155.
Tanaka et al. "Clinically Significant Pharmacokinetic Drug Interactions with Psychoactive Drugs: Antidepressants and Antipsychotics and the Cytochrome p450 System." *J. Clin. Pharm. Ther.* 24(1999):7-16.
Ueda et al. "The Impact of CYP2D6 Genotypes on the Plasma Concentration of Paroxetine in Japanese Psychiatric Patients." *Prog. Neuro-Pysch. Bio. Psych.* 30(2006):486-491.
Marez et al. "Polymorphism of the Cytochrome P450 CYP2D6 Gene in a European Population: Characterization of 48 Mutations and 53 Alleles, Their Frequencies and Evolution." *Pharmacogenetics .* 7(1997):193-202.
Pirmohamed. "Cytochrome P450 Enzyme Polymorphisms and Adverse Drug Reactions." *Toxicol.* 192(2003):23-32.
Viesselman. "Antidepressant and Antimanic Drugs." *Practitioner's Guide to Psychoactive Drugs for Children and Adolescents .* New York: Plenum Publishing Corporation. Werry et al., eds. (1999):249-296.

\* cited by examiner

| | A | B | C | D | E | F |
|---|---|---|---|---|---|---|
| 1 | FACTOR | CATEGORY | | | | |
| 2 | xxx xxxxxx xxx x xxxx xx | xxxxxx | xx | xx | xx | xx |
| 3 | xxx xxxxxx xxx x xxxx xx | xxxxxx | xx | xx | xx | xx |
| 4 | xxxxx xxx x xx x | xxxxxx | xx | xx | xx | xx |
| 5 | xxxxxx xxxx xx | xxxxxx | xx | xx | xx | xx |
| 6 | xxxx | xxxxxx | xx | xx | xx | xx |
| 7 | xx x xxx xx | xxxxxx | xx | xx | xx | xx |
| 8 | xxx xx | xxxxxx | xx | xx | xx | xx |
| 9 | xxxxxxx xxxxx xx xx xxx | xxxxxx | xx | xx | xx | xx |
| 10 | xxx xxxxxx xxx x xxxx xx | xxxxxx | xx | xx | xx | xx |
| 11 | xxx xxx x xxxxx | xxxxxx | xx | xx | xx | xx |
| 12 | xxx xxx | xxxxxx | | xx | xx | xx |
| 13 | xxx x xxx xxxx xx | xxxxxx | xx | xx | xx | xx |
| 14 | xxx xxxx xx x xxx | xxxxxx | xx | xx | xx | xx |

FIG. 3

| LOGIN | PATIENT | CHECK PATIENT | QUESTIONAIRE | SET DRUGS | SET OUTCOMES | MESSAGE | LOGOUT |

PHYSICIAN NAME:
REPORT DESTINATION:
PATIENT NAME:
DATE OF BIRTH:

WHICH OF THE FOLLOWING ISSUES APPLIES TO THE PATIENT?

THE CHILD HAS CHRONIC ILLNESSES OTHER THAN EPILEPSY — NO — 132
THE CHILD HAS A HISTORY OF POOR ADHERENCE — UNK — 134
THE CHILD HAS BEHAVIOR PROBLEMS — NO — 136
THE CHILD HAS LEARNING DIFFICULTIES OR ACADEMIC PROBLEMS — NO — 138
THE CHILD HAS A FAMILY HISTORY OF EPILEPSY OR SEIZURES — NO — 140
THE CHILD'S FAMILY HAS DIFFICULTIES WITH TRANSPORTATION — NO — 142
THE CHILD'S FAMILY HAS EXPERIENCED RECENT STRESSORS — NO — 144
THE CHILD'S PARENT LACKS SOCIAL SUPPORT — UNK — 146
THE CHILD LACKS MEDICAL INSURANCE COVERAGE — NO — 148
THE CHILD HAS MEDICAID — NO — 150

FIG. 13

OPTIMIZATION AND INDIVIDUALIZATION OF MEDICATION SELECTION AND DOSING

CROSS REFERENCE TO RELATED APPLICATIONS

The present application claims the benefit of U.S. Provisional Patent Application Ser. No. 60/740,430, filed Nov. 29, 2005 and of U.S. Provisional Patent Application Ser. No. 60/783,118, filed Mar. 16, 2006, the disclosures of which are incorporated herein by reference.

FIELD OF THE INVENTION

This invention relates to methods for combining a patient's genetic information, a patient's non-heritable host factors and candidate medication characteristics to optimize and individualize medication dosage and compound selection.

BACKGROUND OF THE INVENTION

One of the most important but unresolved problems in therapy with potent and often toxic drugs has been the lack of our ability to describe, understand, and quantify the important mechanistic relationships and variability between drug doses, concentrations in blood, concentrations of metabolites in other body compartments, and the therapeutic and toxic drug effects. For the most part, defining drug action and inter-patient variability has been limited to simplistic, less informative descriptions of average maximum and minimum drug dose requirements that do not permit true individualization of therapy for each patient.

For some drugs over 90% of the measurable variation in selected pharmacokinetic parameters has been shown to be heritable. Traditionally in pharmacokinetic (PK) analysis a series of concentrations over time is measured. A structural model is defined and fit to the data in order to obtain estimates of the desired parameters such as clearance and volume of distribution. The model is fitted to the individual data by using a least squares algorithm that minimizes the difference between observed and the model predicted concentrations. For reasons of simplicity the assumption is made that differences between the observed and predicted concentrations are caused by random error. With this traditional type of analysis, a model is defined for each subject and the individual parameters are then summarized across individuals. However, imprecision in the sample mean and sample standard deviation frequently are greater than expected, while estimates of variability in these parameters are not well characterized.

The FDA is recognizing the importance of the genetic contribution to the inter-individual variation in response to therapy. There has been a significant increase in the number of new drug applications sent to the FDA containing pharmacogenetic information (Wendy Chou, Ph.D./FDA Apr. 3, 2003). Two package inserts reflect this trend. Thioridazine (Mellaril) which is used for neuropsychiatric conditions is contraindicated in patients who are CYP2D6 poor metabolizers; this warning is specifically stated in two places in the insert. Similarly in multiple places in the package insert for Atomoxetine (Strattera, a medication used for ADHD), the association between genetic polymorphisms in drug metabolism and adverse drug reactions is stated.

In certain ethnic groups as many as 10% of the adolescent population have a CYP2D6 haplotype that is associated with poor metabolism of many antidepressant medications. See Wong et al. (2001) *Ann. Acad. Med. Singapore* 29:401-406. Clinical genomic testing of these individuals has clear implications for their treatment and prognosis. In extreme cases, children who were poor metabolizers and who were not identified have had tragic outcomes. These negative case reports have included a reported death of a nine-year-old boy who was not recognized to be a poor CYP2D6 metabolizer. The treatment of this child with fluoxetine continued despite the development of multiple symptoms because these symptoms were not recognized as being related to his extremely high serum levels of fluoxetine. Sallee et al. (2000) *J. Child Adol. Psychiatry* 10(1):27-34.

Adverse drug reactions occur in 28% percent of hospitalized patients and in 17% percent of hospitalized children. In a report by Phillips in JAMA, 27 drugs were most frequently sited in adverse drug reaction reports. 59 percent (16/27) of these drugs were metabolized by at least one enzyme having a poor metabolizer genotype. 37 percent (11/27) were metabolized by CYP2D6, specifically drugs acting on the central nervous system. The annual cost of the morbidity and mortality associated with adverse drug reaction is $177,000,000 dollars (Year 2000 dollars). Clearly drug toxicity is a major health issue with 100,000 deaths a year and 2,000,000 persons suffering permanent disability or prolonged hospitalizations as a result of direct medication adverse reactions.

Although significant inter-individual variability exists in the response to most medications, medication selection and titration is usually empiric rather than individualized. The main reason that physicians do not incorporate genetic and non-heritable host factors responsible for this inter-individual variability into treatment plans is the lack of applicable, easy to use algorithms that translate the patient's characteristics into clinical recommendations. Thus there is a need in the art for a pharmacokinetic dose individualization technique that is informative, cost saving, and effective.

SUMMARY OF THE INVENTION

The present invention is concerned generally with the field of identifying appropriate medications and treatment regimens for a disease based upon genotype in mammals, particularly in humans. It is further concerned with the genetic basis of inter-patient variation in response to therapy, including drug therapy. Specifically, the invention describes the use of gene sequence variances for optimizing efficacy and safety of drug therapy. The invention relates to computerized methods and/or computer-assisted methods for identifying patient population subsets that respond to drug therapy similarly.

The invention provides computerized methods and/or computer-assisted methods of targeting drug therapy, particularly dosing regimens and compound selection to an individual subject or patient. The methods incorporate genetic and non-heritable factors into drug selection and titration. The invention provides computational algorithms for recommending a dosing regimen for a particular patient utilizing population models, genotype information, and clinical information. The methods of the invention allow iterative integration of patient information and clinical data. The methods of the invention provide timely, easy to understand, and easy to implement recommendations. Further the invention provides proactive identification of patients potentially requiring more in depth assessment by a clinical pharmacology specialist.

It is therefore a first aspect of the present invention to provide a computerized method and/or computer-assisted method of selecting a dosing regimen for a patient the method that includes the steps of: (a) integrating patient data with patient associated genotype information; (b) generating a drug concentration profile for the patient; (c) integrating the drug concentration profile and the target drug concentration profile; and (d) providing a dosing regimen for a first compound likely to result in the target drug concentration profile in the subject. In a more detailed embodiment, the method further includes the steps of (x) providing a biological sample; (y) monitoring a biomarker in the biological sample; and (z) integrating the biomarker value with the drug concentration profile information. Alternatively or in addition, the patient data may comprise patient demographic data and clinical data. Alternatively or in addition, the clinical data may include information regarding a second compound, where the second compound may modulate metabolism of the first compound. Alternatively or in addition, the first compound may be a neuropsychiatric medication. Alternatively or in addition, the method may further comprise the step of determining the genotype of a patient at one or more loci of interest.

It is a second object of the present invention to provide a computerized method and/or computer-assisted method for selecting a dosing regimen for a patient, where the method includes the steps of: (a) obtaining patient data; (b) obtaining patient associated genotype information; (c) integrating the patient data with the patient associated genotype information; (d) generating a drug concentration profile for the patient; (e) integrating the drug concentration profile and a target drug concentration profile; (f) providing a dosing regimen for the compound likely to result in the target drug concentration profile in the subject; (g) providing a biological sample from the patient; (h) monitoring a biomarker in the biological sample; (i) integrating the biomarker value with the drug concentration profile information; (j) generating a second drug concentration profile for the patient; (k) supplying a second target drug concentration profile; (l) providing a second dosing regiment for the compound likely to result in the second target drug concentration profile. In addition, the method may further include the step of performing the processes of (f) through (l) at least a second time. Alternatively or in addition, the method may further include the step of selecting a population model for the patient. Alternatively or in addition, the method may further include the step of generating a probability value for a designated response by the patient.

It is a third aspect of the present invention to provide a computerized method and/or computer-assisted method of selecting a dosing regimen for a patient, where the method includes the steps of: (a) generating statistical population models of drug interactions for a plurality of genotypes; (b) obtaining patient associated genotype information; and (c) establishing a dosing regimen by applying the genotype information against the population models. In addition, the step of generating population models may include the use of Bayesian algorithms. Alternatively or in addition, the population models of drug interactions may be defined for a combination of genotypes and non-genetic information.

It is a fourth aspect of the present invention to provide a computerized method and/or computer-assisted method for selecting one or more drugs for a patient that includes the steps of: identifying the phenotype; providing a first plurality of possible medications based upon the identified phenotype; and calculating a ranked list or a predictive index of medications from the first plurality of medications based upon, at least in part, patient specific genetic factors, non-heritable patient factors and drug specific factors. In addition, the calculating step may further consider one or more preclinical toxicity variables, one or more pharmacokinetic variables, one or more clinical efficacy variables, one or more clinical toxicity variables, one or more clinical safety issues, and/or one or more ease of use/adherence variables. In addition, in the calculating step, one or more of the following variables could contribute linearly: TI (therapeutic index–the ratio of (50% lethal dose/50% therapeutic dose)=measure of the drug's inherent toxicity); F (Bioavailability=fraction of the dose which reaches the systemic circulation as intact drug); fu (the extent to which a drug is bound in plasma or blood is called the fraction unbound=[unbound drug concentration/[total drug concentration]); f-BIND-T (fraction of drug that is a substrate for a drug-specific efflux transporter "T"); MET-L (drug with linear metabolism); f-MET-E (fraction of drug that is metabolized by drug metabolizing enzyme "E"); PEX (percentage of drug metabolizing enzyme "E" with functional polymorphism "X"); $CL_{cr}$ (creatinine clearance=the volume of blood cleared of creatinine per unit time=(liters/hour)); IDR (rate of idiosyncratic reactions); FORM (formulation); FREQ (frequency of daily drug administration); MAT ED (maternal education level); SES (socio-economic class); and TRANS (method of transportation to/from clinic). Alternatively or in addition, in the calculating step, one or more of the following variables could contribute exponentially: ATA (number of functional non-wild type transporter polymorphisms for the specific patient); MET-NonL (drug with non-linear metabolism); AEA (number of functional non-wild type drug metabolizing enzyme polymorphisms for the specific patient); MED-IND (concurrent use of medications that induce metabolizing enzymes); MED-INH (concurrent use of medications that inhibit metabolizing enzymes); DIET-IND (concurrent use of dietary supplements that induce metabolizing enzymes); DIET-INH (concurrent use of dietary supplements that inhibit metabolizing enzymes); NNT-EFF (number need to treat=number of patients who need to be treated to reach 1 desired outcome); META-EEF (results from an efficacy meta-analysis of clinical trials involving medications used to treat a neuropsychiatric disorder); NNT-TOX (number need to treat=number of patients who need to be treated to have a 1 toxicity outcome); and META-TOX (results from toxicity meta-analysis of clinical trials involving medications used to treat a neuropsychiatric disorder).

In another alternative detailed embodiment of the fourth aspect of the present invention, the calculating step may involve linear algebra computational science to integrate disease specific evidence based medicine data, drug specific basic pharmacology characteristics, patient specific advanced pharmacology principles, and/or patient specific environmental and genetic factors to produce a ranking of potential medications. In addition, or alternatively, the calculating step may assign, for each potential medication, computational values corresponding to a favorability of utilizing the potential medication for a corresponding plurality of factors. In addition, the plurality of factors may include factors from a plurality of the following categories: disease specific evidence based medicine data, drug specific basic pharmacology characteristics, patient specific advanced pharmacology principles, patient specific environmental and patient specific genetic factors. Alternatively or in addition, the plurality of computational values may include positive values for favorable factors and negative values for unfavorable factors, and the calculating step involves adding the computational values to determine a score. Alternatively or in addition, the plurality of computational values may include positive values for favorable factors and negative values for unfavorable factors and weights corresponding to the relative importance of such factors, and the calculating step involves adding the weighted computational values to determine a score.

In yet another alternate detailed embodiment of the invention, the computerized method may further comprise a step of generating an adherence score corresponding to a predicted likelihood that the patient will adhere to a scheduled therapy or prescription.

It is a fifth aspect of the present invention to provide a computerized method and/or computer-assisted method for selecting a starting dose of a medication for a patient that includes the steps of: for a given medication, determining if the patient is an extensive metabolizer for the medication, an intermediate metabolizer for the medication, or a poor metabolizer for the medication; calculating the starting dose based upon, at least in part, a usual drug dose for a given population ($D_{pop}$), the frequency of extensive metabolizers in the given population ($f_{EM}$), the frequency of intermediate metabolizers in the given population ($f_{IM}$) and/or the frequency of poor metabolizers in the general population ($f_{PM}$); and determining a minimal dose adjustment unit for the medication based, at least in part, upon the patient's genetic information. In addition, the step of determining if the patient may be an extensive metabolizer for the medication, an intermediate metabolizer for the medication, or a poor metabolizer for the medication is based, at least in part, upon the patient's genetic information. Alternatively or in addition, (a) the percent of the usual drug dose $D_{pop}$ for an extensive metabolizer $D_{EM}$ is $$D_{EM}=100/(f_{EM}+f_{IM}\cdot S+f_{PM}\cdot R)$$

where S is the Area Under the Time Concentration Curve for extensive metabolizer subpopulation divided by the Area Under the Time Concentration Curve for intermediate metabolizer subpopulation, and where R is the Area Under the Time Concentration Curve for extensive metabolizer subpopulation divided by the Area Under the Time Concentration Curve for poor metabolizer subpopulation; (b) the percent of the usual drug dose $D_{pop}$ for a poor metabolizer $D_{PM}$ is $$D_{PM}=R\cdot D_{EM}; \text{ and}$$

(c) the percent of the usual drug dose $D_{pop}$ for an intermediate metabolizer $D_{IM}$ is $$D_{IM}=S\cdot D_{EM}$$

Alternatively or in addition, the minimal dose adjustment unit for the medication may be based, at least in part, upon a number of non-functional alleles, $D_{EM}$, $D_{IM}$, and/or $D_{PM}$.

It is a sixth aspect of the present invention to provide a computerized method and/or computer-assisted method for selecting one or more drugs for a patient that includes the steps of: identifying the phenotype; providing a first plurality of possible medications based upon the patient's diagnosis; and calculating a ranked list or a predictive index of medications from the first plurality of medications based upon, at least in part, patient specific genetic factors, non-heritable patient factors and drug specific factors. In addition, the calculating step may involve linear algebra computational science to integrate disease specific evidence based medicine data, drug specific basic pharmacology characteristics, patient specific advanced pharmacology principles, and/or patient specific environmental and genetic factors to produce a ranking of potential medications. Alternatively or in addition, the calculating step assigns, for each potential medication, computational values corresponding to a favorability of utilizing the potential medication for a corresponding plurality of factors, where the plurality of factors may include factors from a plurality of the following categories: disease specific evidence based medicine data, drug specific basic pharmacology characteristics, patient specific advanced pharmacology principles, patient specific environmental and patient specific genetic factors. Alternatively or in addition, the plurality of computational values include positive values for favorable factors and negative values for unfavorable factors, and the calculating step involves adding the computational values to determine a score, where the plurality of computational values may include positive values for favorable factors and negative values for unfavorable factors and weights corresponding to the relative importance of such factors, and the calculating step involves adding the weighted computational values to determine a score.

In another detailed embodiment of the sixth aspect of the present invention, the method may include a step of generating an adherence score corresponding to a predicted likelihood that the patient will adhere to a scheduled therapy or prescription.

It is a seventh aspect of the present invention to provide a computer, a computer system or a computerized tool designed and programmed to perform any or all of the above computer implemented methods. In addition, the computer, computer system or computerized tool may provide a graphical user interface to provide for the collection of appropriate data from users, such as any of the above-discussed factors. Alternatively, or in addition, the computer, computer system or computerized tool may provide a graphical user interface (or any other known computer output, such as a printout) to provide the report, analysis, recommendation or any other output resulting from any of the above-discussed methods.

BRIEF DESCRIPTION OF THE DRAWINGS

FIG. 3 is an example (very small) segment of a disease matrix for use with an exemplary embodiment of the invention.

FIG. 13 is a screen shot illustrating another step of an exemplary computer implemented method of the present invention.

DETAILED DESCRIPTION OF THE INVENTION

Figure 1:
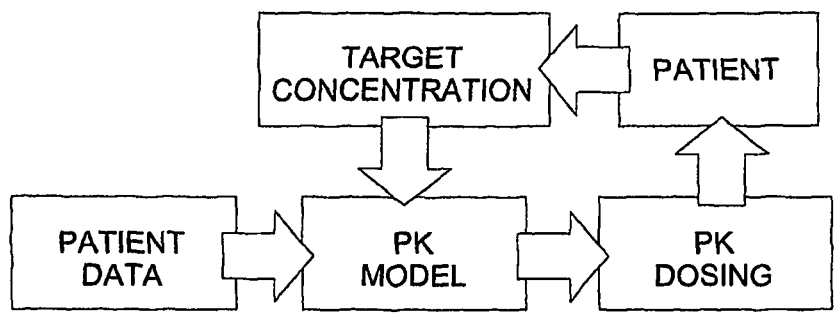
FIG. 1 presents a schematic depiction of the processes involved in a method selecting a dosing regimen for an individual patient.

Defining and describing the often complex relationships of drug action and inter-patient variability has historically been very difficult. Developing pharmacokinetic (PK) and pharmacodynamic (PD) models of these variables provides a method of defining and describing the relationships between drug action and patient variability. Further drug or compound actions (effects) are directly related to the drug concentration at the site(s) of action. There is usually a better relationship between the effect of a given drug and its concentration in the blood than between the dose of the drug given and the effect.

The invention provides population models for various compounds that incorporate pharmacokinetic and pharmacodynamic models of drug action and interpatient variability. Further the invention provides computerized methods and/or computer-assisted methods (including software algorithms) that utilize the one or more population models of the invention to predict a dosing regimen for a particular compound or to predict patient response to a compound. The computerized methods and/or computer-assisted methods (including software algorithms) of the invention generate a prediction regarding a subject's ability to metabolize a compound of interest. The computerized methods and/or computer-assisted methods (including software algorithms) of the invention provide for iterative evaluation of a patient's response to a dosing regimen or compound incorporating data obtained from monitoring at least one suitable biomarker. Often subjects receive more than one medication. These additional medications may affect the subject's ability to metabolize a compound of interest. Thus, in an embodiment computerized methods and/or computer-assisted methods (including software algorithms) of the invention provide a means of integrating information regarding such an additional compound or compounds and the effects of such an additional compound on the subject's ability to metabolize a compound of interest.

A "compound" comprises, but is not limited to, a drug, medication, agent, therapeutically effective agent, neuropsychiatric medications, neurotransmitter inhibitors, neurotransmitter receptor modulators, G-proteins, G-protein receptor inhibitors, ACE inhibitors, hormone receptor modulators, alcohols, reverse transcriptase inhibitors, nucleic acid molecules, aldosterone antagonists, polypeptides, peptides, peptidomimetics, glycoproteins, transcription factors, small molecules, chemokine receptors, antisense nucleotide sequences, chemokine receptor ligands, lipids, antibodies, receptor inhibitors, ligands, sterols, steroids, hormones, chemokine receptor agonists, chemokine receptor antagonists, agonists, antagonists, ion-channel modulators, diuretics, enzymes, enzyme inhibitors, carbohydrates, deaminases, deaminase inhibitors, hormones, phosphatases, lactones, and vasodilators. A compound may additionally comprise a pharmaceutically acceptable carrier.

Neuropsychiatric medications include, but are not limited to, antidepressants, mood elevating agents, norepinephrine-reuptake inhibitors, tertiary amine tricyclics, amitriptyline, clomipramine, doxepin, imipramine, secondary amine tricyclics amoxapine, desipramine, maprotiline, protriptyline, nortriptyline, selective serotonin-reuptake inhibitors (SSRIs), fluoxetine, fluvoxamine, paroxetine, sertraline, citalopram, escitalopram, venlafaxine, atypical antidepressants, bupropion, nefazodone, trazodone; noradrenergic and specific serotonergic antidepressants, mirtazapine, monoamine oxidase inhibitors, phenelzine, tranylcypromine, selegiline; antipsychotic agents, tricyclic phenothiazines, chlorpromazine, triflupromazine, thioridazine, mesoridazine, fluphenazine, trifluoperazine, thioxanthenes, chlorprothixene, clopenthixol, flupenthixol, piflutixol, thiothixene, dibenzepines, loxapine, clozapine, clothiapine, metiapine, zotapine, fluperlapine, olanzapine, butyrophenones, haloperidol, diphenylbutylpiperidines, fluspirilene, penfluridol, pimozide, haloperidol decanoate, indolones, neuroleptics, anti-anxiety/sedative agents, benzodiazepines, chlordiazepoxide, diazepam, oxazepam, clorazepate, lorazepam, prazepam, alprazolam, and halazepam; mood stabilizing agents, lithium salts, valproic acid; attention deficit hyperactivity disorder agents, dextroamphetamine, methylphenidate, pemoline, and atomoxetine; anticonvulsants, phenobarbital, phenytoin, carbamazepine, valproic acid, felbamate, gabapentin, tiagabine, lamotrigine, topiramate, zonisamide, oxcarbazepine, levetiracetam, pregabalin, ethotoin, and peganone; headache medications, ibuprofen, aspirin/acetometaphen/caffeine, diclofenac, ketoprofen, ketorolac, flurbiprofen, meclofenamate, naproxen, ergotamine tartrate, dihydroergotamine, ergotamine, acetometaphen/isometheptene mucate/dichloralphenazone, sumatriptan succinate, zolmitriptan, rizatriptan, naratriptan hydrochloride, almotriptan, frovatriptan, eletriptan, diclofenac, fenoprofen, flurbiprofen, kepaprofen, naproxen sodium, amitriptyline, desipramine, doxepin, imipramine, nortriptyline, fluoxetine, paroxetine, sertraline, venlafaxine, trazodone, bupropion, atenolol, metoprolol, nadolol, propranolol, timolol, diltiazem, nicardipine, nifedipine, nimodipine, verapamil, divalproex sodium, gabapentin, valproic acid, and topiramate; and dementia medications, tacrine, donepezil, galantamine, galanthamine, rivastigmine, and memantine.

By "drug" is intended a chemical entity, biological product, or combination of chemical entities or biological products administered to a person to treat, prevent, or control a disease or condition. The term "drug" may include, without limitation, agents that are approved for sale as pharmaceutical products by government regulatory agencies such as the U.S. Food and Drug Administration, European Medicines Evaluation Agency, agents that do not require approval by a government regulatory agency, food additives or supplements including agents commonly characterized as vitamins, natural products, and completely or incompletely characterized mixtures of chemical entities including natural agents or purified or partially purified natural products. It is understood that the methods of the invention are suitable for use with any of the drugs or compounds in the 2005 Physicians Desk Reference, Thomson Healthcare 59$^{th}$. ed., herein incorporated by reference in its entirety.

The computerized methods and/or computer-assisted methods (including software algorithms) of the invention utilize subject or patient associated genotype information. The term "genotype" refers to the alleles present in genomic DNA from a subject or patient where an allele can be defined by the particular nucleotide(s) present in a nucleic acid sequence at a particular sites(s). Often a genotype is the nucleotide(s) present at a single polymorphic site known to vary in the human population. By "genotype information" is intended information pertaining to variances or alterations in the genetic structure of a gene or locus of interest. Genotype information may indicate the presence or absence of a predetermined allele. A "loci of interest" may be a gene, allele, or polymorphism of interest. Genes or loci of interest include genes that encode a) medication specific metabolizing enzymes, b) medication specific transporters, c) medication specific receptors, d) enzymes, transporters or receptors affecting other drugs that interact with the medication in question or e) body functions that affect that activities of the medication in question. In an embodiment of the invention loci of interest include, but are not limited to, five cytochrome P450 genes, the serotonin transporter gene, the dopamine transporter gene, and the dopamine receptor genes. The five cytochrome P450 genes can encode CYP2D6, CYP1A2, CYP2C19, CYP2C9 and CYP2E1. Alleles of particular interest include, but are not limited to, the CYP1A2*1A or 1A2*3 allele, the CYP2C19*1A, 2C19*1B, or 2C19*2A allele, and the CYP2D6*1A, 2D6*2, 2D6*2N, 2D6*3, 2D6*4, 2D6*5, 2D6*6, 2D6*7, 2D6*8, 2D6*10, 2D6*12, or 2D6*17 allele. The serotonin receptor genes encode serotonin receptors 1A, 1B, 1D, 2A, or 2C and the dopamine receptor genes encode dopamine receptors D1, D2, D3, D4, D5, and D6. The serotonin transported gene is also an important part of the genotype. Additional genes, alleles, polymorphisms, and loci of interest are presented in Tables 1 and 2.

TABLE 1

Cytochrome P450 genes

| Cytochrome P450 Gene | Allele | Polymorphism |
|---|---|---|
| 1A1 | *1A | None |
|  | *2 | A2455G |
|  | *3 | T3205C |
|  | *4 | C2453A |
| 1A2 | *1A | None |
|  | *IF | −164C > A |
|  | *3 | G1042A |
| 1B1 | *1 | None |
|  | *2 | R48G |
|  | *3 | L432V |
|  | *4 | N453S |
|  | *11 | V57C |
|  | *14 | E281X |
|  | *18 | G365W |
|  | *19 | P379L |
|  | *20 | E3 87K |
|  | *25 | R469W |
| 2A6 | *1A | None |
|  | *1B | CYP2A 7 translocated to 3' - end |
|  | *2 | T479A |
|  | *5 | *1B + G6440T |
| 2B6 | *1 |  |
|  | *1'2 | R22C |
|  | *1'3 | S259C |
|  | *4 | K262R |
|  | *5 | R487C |
|  | *6 | Q172H; K262R |
|  | *7 | Q172H; I < 262R; R487C |
| 2C8 | *1A | None |
|  | *1B | −271C > A |
|  | *1C | −370T > G |
|  | *2 | I269F |

TABLE 1-continued

Cytochrome P450 genes

| Cytochrome P450 Gene | Allele | Polymorphism |
|---|---|---|
|  | *3 | R139K; K399R |
|  | *4 | I264M |
| 2C9 | *1 | None |
|  | *2 | R144C |
|  | *3 | I359L |
|  | *5 | D360E |
| 2C18 | rot | T204A |
|  | m2 | A460T |
| 2C19 | *1A | None |
|  | *IB | I331V |
|  | *2A | Splicing defect |
|  | *2B | Splicing defect; E92D |
|  | *3 | New stop codon 636G > A |
|  | *4 | GTG initiation codon, 1A > G |
|  | *5(A, B) | 1297C > T, amino acid change (R433W) |
|  | *6 | 395G > A, amino acid change (R132Q) |
|  | *7 | IVS5 + 2T > A, splicing defect |
|  | *8 | 358T > C, amino acid change (W120R) |
| 2D6 | *IA | None |
|  | *2 | G1661C, C2850T |
|  | *2N | Gene duplication |
|  | *3 | A2549 deletion |
|  | *4 | G1846A |
|  | *5 | Gene deletion |
|  | *6 | T1707 deletion |
|  | *7 | A2935C |
|  | *8 | G1758T |
|  | *10 | C100T |
|  | *12 | G124A |
|  | *17 | C1023T, C2850T |
|  | *35 | G31A |
| 2E1 | *IA | None |
|  | *IC, *1D | (6 or 8 bp repeats) |
|  | *2 | G1132A |
|  | *4 | G476A |
|  | *5 | G(−1293)C |
|  | *5 | C(−1053)T |
|  | *7 | T(−333)A |
|  | *7 | G(−71)T |
|  | *7 | A(−353)G |
| 3A4 | *IA | None |
|  | *IB | A(−392)G |
|  | *2 | Amino acid change (S222P) |
|  | *5 | Amino acid change (P218R) |
|  | *6 | Frameshift, 831 ins A |
|  | *12 | Amino acid change (L373F) |
|  | *13 | Amino acid change (P416L) |
|  | *15A | Amino acid change (R162Q) |
|  | *17 | Amino acid change (F189S, Decreased) |
|  | *18A | Amino acid change (L293P, increased) |
| 3A5 | *1A | None |
|  | *3 | A6986G |
|  | *5 | T12952C |
|  | *6 | G14960A |

TABLE 2

Non-Cytochrome P450 genes

| Gene | Symbol | Polymorphism |
|---|---|---|
| Dopamine Transporter | DAT1, SLC6A3 | 40 bp VNTR 10 repeat allele G710A, Q237R C124T, L42F |
| Dopamine Receptor D1 | DRD1 | DRD 1 B2 T244G |

TABLE 2-continued

Non-Cytochrome P450 genes

| Gene | Symbol | Polymorphism |
|---|---|---|
| | | C179T |
| | | G127A |
| | | T11G |
| | | C81T |
| | | T5950, S199A |
| | | G150T, R50S |
| | | C1100, T37R |
| | | A109C, T37P |
| Dopamine Receptor D2 | DRD2 | TaqI A |
| | | A1051G, T35A |
| | | C932G, S311 C |
| | | C928, P31 OS |
| | | G460A, V1541 |
| Dopamine Receptor D3 | DRD3 | Ball in exon I |
| | | MspI |
| | | DRD31 |
| | | Gly/Ser (allele 2) |
| | | A250, S9G |
| Dopamine Receptor D4 | DRD4 | 48 repeat in exon 3 |
| | | 7 repeat allele. |
| | | 12/13 bp insertion/deletion |
| | | T581G, V194G |
| | | C841G, P281A |
| Dopamine Receptor D5 | DRD5 | T978C |
| | | L88F |
| | | A889C, T297P |
| | | G1252A, V4181 |
| | | G181A, V61M |
| | | G185C, C62S |
| | | T2630, R88L |
| | | G1354A, W455 |
| Tryptophan Hydroxylase | TPH | A218C |
| | | A779C |
| | | G-5806T |
| | | A-6526G |
| | | (CT)m(CAMCT)p allele 194 in 3'UTR, 5657 bp distant from exon 11 |
| Serotonin Transporter | 5-HTTR | Promoter repeat (44 bp insertion (L)/deletion(S) (L = Long form; S = ShOli form) |
| | | Exon 2 variable repeat |
| | | A1815C |
| | | G603C |
| | | G167C |
| Serotonin Receptor 1A | HTR1A | RsaI |
| | | G815A, G272D |
| | | G656T, R219L |
| | | C548T, P551L |
| | | A82G, 128V |
| | | G64A, |
| | | G22S |
| | | C47T, P16L |
| Serotonin Receptor 1B | HTR1B | G86IC |
| | | G86lC, V287V |
| | | T371G, F124C |
| | | T655C, F219L |
| | | A1099G, I367V |
| | | G1120A, E374K |
| Serotonin Receptor lD | HTR1D | G506T |
| | | Cl73T |
| | | C794T, S265L |
| Serotonin Receptor 2A | HTR2A | C74A |
| | | T102C |
| | | T516C |
| | | C1340T |
| | | C1354T |
| Serotonin Receptor 2C | HTR2C | G796C |
| | | ClOG, L4V |
| | | G68C, C23S |
| Catechol-o-methyltransferase | COMT | G158A (Also known as Val/Met) |
| | | G214T |
| | | A72S |
| | | G101C |
| | | C34S |
| | | G473A |

In an embodiment of the invention, the computerized methods and/or computer-assisted methods (including software algorithms) are utilized to select a dosing regimen for a patient in need of a neuropsychiatric medication. A major gene in the neuropsychiatric panel is CYP2D6. Substrates of CYP2D6 typically are weak bases with the cationic binding site located away from the carbon atom to be oxidized. In particular, substrates of CYP2D6 include amitriptyline, nortriptyline, haloperidol, and desipramine. Some individuals have altered CYP2D6 gene sequences that result in synthesis of enzymes devoid of catalytic activity or in enzymes with diminished catalytic activity. These individuals metabolize SSRIs and tricyclic antidepressants (TCAs) poorly. Duplication/multiplication of the functional CYP2D6 gene also has been observed and results in ultrarapid metabolism of SSRIs and other drugs. Individuals without inactivating polymorphisms, deletions, or duplications have the phenotype of an extensive drug metabolizer and are designated as CYF2D6*1. The CYP2D6*3 and *4 alleles account for nearly 70% of the total deficiencies that result in the poor metabolizer phenotype. The polymorphism responsible for CYP2D6*3 (2549A>del) produces a frame-shift in the mRNA. A polymorphism involved with the CYP2D6*4 allele (1846G>A) disrupts mRNA splicing. These changes produce truncated forms of CYP2D6 devoid of catalytic activity. Other poor metabolizers are CYP2D6*5, *10, and *17. CYP2D6*5 is due to complete gene deletion. The polymorphisms in CYF2D6*10 and *17 produce amino acid substitutions in the CYP2D6 enzyme which have decreased enzyme activity. All of these polymorphisms are autosomal co-dominant traits. Only individuals who are homozygous or who are compound heterozygous for these polymorphisms are poor metabolizers. Individuals who are heterozygous, with one normal gene and one polymorphic gene, will have metabolism intermediate between the extensive (normal) and poor metabolizers. Individuals who are heterozygous for duplication/multiplication alleles are ultra-rapid metabolizers.

CYP1A2 metabolizes many aromatic and heterocyclic anilines including clozapine and impraniline. The CYP1A2*IF allele can result in a product with higher inducibility or increased activity. (See Sachse et al. (1999) *Br. J. Clin. Pharmacol.* 47: 445-449). CYP2C19 also metabolizes many substrates including imipramine, citalopram, and diazepam. The CYP2C19 *2A, *2B, *3, *4, *5A, *5B, *6, *7, and ':'8 alleles encode products with little or no activity. See Theanu et al. (1999) *J. Pharmacol. Exp. Ther.* 290: 635-640.

CYP1A1 can be associated with toxic or allergic reactions by extra-hepatic generation of reactive metabolites. CYP3A4 metabolizes a variety of substrates including alprazolam. CYP1B1 can be associated with toxic or allergic reactions by extra-hepatic generation of reactive metabolites and also metabolizes steroid hormones (e.g., 17-estradiol). Substrates for CYP2A6 and CYP2B6 include valproic acid and bupropion, respectively. Substrates for CYP2C9 include Tylenol and antabuse (disulfuram). Substrates for CYP2E1 include phenytoin and carbamazepine. Decreases in activity in one or more of the cytochrome P450 enzymes can impact one or more of the other cytochrome P450 enzymes.

Methods of determining genotype information are known in the art. Genotype information obtained by any method of determining genotype known in the art may be employed in the practice of the invention. Any means of determining genotype known in the art may be used in the methods of the invention.

Generally genomic DNA is used to determine genotype, although mRNA analysis has been used as a screening method in some cases. Routine, commercially available methods can be used to extract genomic DNA from a blood or tissue sample such as the QIAamp@ Tissue Kit (Qiagen, Chatsworth, Calif.), Wizard@ Genomic DNApurificationldt (Promega) and the A.S.A.P.™ Genomic DNA isolation lat (Boebringer Mannheim, Indianapolis, Ind.).

Typically before the genotype is determined, enzymatic amplification of the DNA segment containing the loci of interest is performed. A common type of enzymatic amplification is the polymerase chain reaction (PCR). Known methods of PCR include, but are not limited to, methods using paired primers, nested primers, single specific primers, degenerate primers, gene-specific primers, vector-specific primers, partially-mismatched primers, and the like. Known methods of PCR include, but are not limited to, methods using DNA polymerases from extremophiles, engineered DNA polymerases, and long-range PCR. It is recognized that it is preferable to use high fidelity PCR reaction conditions in the methods of the invention. See also Innis et al., eds. (1990) *PCR Protocols: A Guide to Methods and Applications* (Academic Press, New York); Innis and Gelfand, eds. (1995) *PCR Strategies* (Academic Press, New York); Innis and Gelfand, eds. (1999) *PCR Methods Manual* (Academic Press, New York); and *PCR Primer: A Laboratory Manual*, Ed. by Dieffenbach, C. and Dveksler, G., Cold Spring Harbor Laboratory Press, 1995. Long range PCR amplification methods include methods such as those described in the TaKaRa LA PCR guide, Takara Shuzo Co., Ltd.

When using RNA as a source of template, reverse transcriptase can be used to synthesize complementary DNA (cDNA) strands. Ligase chain reaction, strand displacement amplification, self-sustained sequence replication or nucleic acid sequence-based amplification also can be used to obtain isolated nucleic acids. See, for example, Lewis (1992) *Genetic Engineering News* 12(9): 1; Guatelli et al. (1990) *Proc. Natl. Acad. Sci. USA* 87:1874-1878; and Weiss (1991) *Science* 254:12921293.

Methods of determining genotype include, but are not limited to, direct nucleotide sequencing, dye primer sequencing, allele specific hybridization, allele specific restriction digests, mismatch cleavage reactions, MS-PCR, allele-specific PCR, and commercially available kits such as those for the detection of cytochrome P450 variants (TAG-IT™ kits are available from Tm Biosciences Corporation (Toronto, Ontario). See, Stoneking et al., 1991, *Am. J. Hmn. Genet.* 48:370-382; Prince et al, 2001, *Genome Res.* 11(1):152-162; and Myakishev et al., 2001, *Genome* 11(1):163-169.

Additional methods of determining genotype include, but are not limited to, methods involving contacting a nucleic acid sequence corresponding to one of the loci of interest or a product of such a locus with a probe. The probe is able to distinguish a particular form of the gene or the gene product, or the presence of a particular variance or variances for example by differential binding or hybridization. Thus, exemplary probes include nucleic acid hybridization probes, peptide nucleic acid probes, nucleotide-containing probes that also contain at least one nucleotide analog, and antibodies, such as monoclonal antibodies, and other probes. Those skilled in the art are familiar with the preparation of probes with particular specificities. One of skill in the art will recognize that a variety of variables can be adjusted to optimize the discrimination between variant forms of a gene including changes in salt concentration, pH, temperature, and addition of various agents that affect the differential affinity of base pairing (see Ausubel et al., eds. (1995) *Current Protocols in Molecular Biology*, (Greene Publishing and Wiley-Interscience, New York).

The exemplary computerized methods and/or computer-assisted methods (including software algorithms) of the invention may employ the following rationale. The pharmacokinetic characteristics of a compound, particularly a neuropsychiatric drug, affect the initial dose of a compound more than the compound's pharmacodynamic properties. A compound's pharmacokinetic profile is a dynamic summation of its absorption, distribution, metabolism, and excretion. Genetic differences in drug metabolizing enzymes (DME) that affect enzyme activity and thus drug metabolism constitute a major component of most compounds' pharmacokinetic variability. DMEs include, but are not limited to, a) medication specific metabolizing enzymes, b) medication specific transporters, c) medication specific receptors, d) enzymes, transporters or receptors affecting other drugs that interact with the medication in question or e) body functions that affect that activities of the medication in question. Most compounds' absorption, distribution, and excretion characteristics are independent of the genetic variability in DME activity. Specific DME polymorphisms affect the metabolism of most compounds in a reproducible, predictable, uniform manner. Typically a detectable polymorphism in a specific DME will either have no effect or will reduce enzyme activity. Thus, the subject will have either:

1. two functional alleles (a wild-type, normal, or extensive metabolizer);
2. one functional allele (an intermediate metabolizer); or
3. no functional alleles (a poor metabolizer).

Additionally for certain genes, such as CYP2D6, multiple copies of the gene may be present. In such instances, the presence of more than two functional alleles for a particular gene correlates with an ultrarapid metabolizer state.

Frequently more than one DMEs working either in series or in parallel metabolize a particular compound. The effect of genetic variability for each DME can be determined independently and combined. The invention provides methods of combining or integrating the genetic variability effect for each DME or DMEs that function sequentially or concurrently. The methods of the invention utilize Bayesian population pharmacokinetic modeling and analysis to integrate and predict the effects of multiple DMEs on metabolism of a particular compound.

Also, the concurrent use of more than one compound can affect the activity of a subject's DMEs. Again, the effect of genetic variability for each DME can be determined independently for each compound. The computerized methods and/or computer-assisted methods (including software algorithms) of the invention utilize Bayesian population pharmacokinetic modeling and analysis to integrate and predict the effects of multiple compounds on one or more DMEs. The methods of the invention allow the integration of information about the genetic variability of one or more DMEs and one or more compounds to generate an area under the time concentration curve (AUC) value. The AUC value reflects the amount of a particular compound accessible to a patient and is the clinically important variable.

The AUC value is determined by drug dose and patient specific pharmacokinetics. Prior to this invention, medical practice utilized a "one size fits all" approach that kept the drug dose constant. In the "one size fits all" approach, variability in pharmacokinetics among patients leads to variability in AUC that results in interpatient clinical variability such as side effects or variable efficacy levels. Thus the methods of the invention provide a means of selecting compound dosing regimens that provide patients with similar AUC values. The methods of the invention integrate the number of genetic variations to be included, the population frequency for each genetic variation, and AUC data for each genetic variation. The methods of the invention transforms a heterogenous population into multiple homogenous subpopulations. Such homogenous subpopulations, suitable dosing regimens, and suitable compounds can be described in a population profile of the invention.

By "dosing regimen" is intended a combination of factors including "dosage level" and "frequency of administration". An optimized dosing regimen provides a therapeutically reasonable balance between pharmacological effectiveness and deleterious effects. A "frequency of administration" refers to how often in a specified time period a treatment is administered, e.g., once, twice, or three times per day, every other day, every other week, etc. For a compound or compounds of interest, a frequency of administration is chosen to achieve a pharmacologically effective average or peak serum level without excessive deleterious effects. Thus, it is desirable to maintain the serum level of the drug within a therapeutic window of concentrations for a high percentage of time.

The exemplary software program of the invention employs Bayesian methods. The Bayesian methods allow fewer drug measurements for individual PK parameter estimation, sample sizes (e.g. one sample), and random samples. Therapeutic drug monitoring data, when applied appropriately, can also be used to detect and quantify clinically relevant drug-drug interactions. These methods are more informative, cost-saving, and reliable than methods relying on simply reporting results as below, within or above a published range.

Determining a Predictive Index Called the "Simplicity Index"

Definitions:

The following abbreviations and definitions will be used in the construction of the simplicity index—the variables are grouped by common themes:

Preclinical Toxicity Variables
1. TD50=called "50% therapeutic dose"=the dose of the medication that results in 50% of the animals tested achieving the desired therapeutic outcome
2. LD50=called "50% lethal dose"=the dose of the medication that results in 50% of the animals tested dying
3. TI=called therapeutic index=the ratio of LD50/TD50=a measure of the drug's inherent toxicity Pharmacokinetic Variables
4. F=Bioavailability=fraction of the dose which reaches the systemic circulation as intact drug
5. fu=The extent to which a drug is bound in plasma or blood is called the fraction unbound=[unbound drug concentration]/[total drug concentration]
6. f-BIND-T=fraction of drug that is a substrate for a drug-specific efflux transporter "T"
7. PTX=percentage of transporter "T" with functional polymorphism "X"
8. ATA=number of functional non-wild type transporter polymorphisms for the specific patient
9. MET-NonL=drug with non-linear metabolism
10. MET-L=drug with linear metabolism
11. f-MET-E=fraction of drug that is metabolized by drug metabolizing enzyme "E"
12. PEX=percentage of drug metabolizing enzyme "E" with functional polymorphism "X"
13. AEA=number of functional non-wild type drug metabolizing enzyme polymorphisms for the specific patient
14. AUC=.Total area under the plasma drug concentration-time curve=mg*hour/L
15. CL=clearance=the volume of blood cleared of drug per unit time=(liters/hour), CL=dose/AUC
16. $CL_{cr}$=creatine clearance=the volume of blood cleared of creatinine per unit time=(liters/hour)
17. MED-IND=concurrent use of medications that induce metabolizing enzymes
18. MED-INH=concurrent use of medications that inhibit metabolizing enzymes
19. DIET-IND=concurrent use of dietary supplements that induce metabolizing enzymes
20. DIET-INH=concurrent use of dietary supplements that inhibit metabolizing enzymes Clinical Efficacy Variables
21. NNT-EFF=number need to treat=the number of patients who need to be treated to reach 1 desired outcome
22. OR=odds ratio=a measure of the degree of association; for example, the odds of reaching the desired outcome among the treated cases compared with the odds of not reaching the desired outcome among the controls
23. META-EFF=results from an efficacy meta-analysis of clinical trials involving medications used to treat a neuropsychiatric disorder Clinical Toxicity Variables
24. NNT-TOX=number need to treat=the number of patients who need to be treated to have 1 toxicity outcome
25. OR=odds ratio=a measure of the degree of association; for example, the odds of reaching the drug toxicity among the treated cases compared with the odds of not reaching drug toxicity among the controls
26. META-TOX=results from a toxicity meta-analysis of clinical trials involving medications used to treat a neuropsychiatric disorder Clinical Safety Issues
27. IDR=rate of idiosyncratic reactions Ease of Use/Adherence Variables
28. FORM=formulation
29. FREQ=frequency of daily drug administration
30. MAT ED=maternal education level
31. SES=socio-economic class
32. TRANS=method of transportation to/from clinic An algorithm can be used to rank the most appropriate medications for an individual patient. The design of the algorithm requires the initial identification of the phenotype, which provides a preliminary identification of the universe of possible medications. At the next step of the algorithm, the results of the target gene analyses can be sequentially entered. The algorithm that produces the predictive index (called the "simplicity index") combines the above factors using the following principles:
1. Each factor contributes differentially based on weighting and scaling variables determined during the validation process.

2. The following variables contribute linearly to the final ranking score: TI, F, fu, f-BIND-T, MET-L, f-MET-E, PEX, $CL_{cr}$, IDR, FORM, FREQ, MAT ED, SES, TRANS
3. The following variables contribute exponentially to the final ranking score: ATA, MET-NonL, AEA, MED-IND, MED-INH, DIET-IND, DIET-INH, NNT-EFF, META-EEF, NNT-TOX, META-TOX The algorithm produces a rank list of medications based on the above patient specific genetic factors, non-heritable patient factors and drug specific factors. An exemplary software tool for determining such a predictive index, called the "simplicity index," is described in detail below.

Determining Initial Starting Dose

The following abbreviations and definitions will be used in the determination of the initial starting dose:

Abbreviations:

$D_{pop}$=the perceived usual drug dosage for the general population

Extensive Metabolizers

EM=extensive metabolizer $f_{EM}$=frequency of extensive metabolizers in the general population $D_{EM}$=Drug dosage for extensive metabolizer subpopulation $AUC_{EM}$=Area Under the Time Concentration Curve for extensive metabolizer subpopulation Intermediate Metabolizers IM=intermediate metabolizer $f_{IM}$=frequency of intermediate metabolizers in the general population $D_{IM}$=Drug dosage for intermediate metabolizer subpopulation $AUC_{IM}$=Area Under the Time Concentration Curve for intermediate metabolizer subpopulation Poor Metabolizers PM=poor metabolizer $f_{PM}$=frequency of poor metabolizers in the general population $D_{PM}$=Drug dosage for poor metabolizers subpopulation $AUC_{PM}$=Area Under the Time Concentration Curve for poor metabolizers subpopulation The following section describes how the dosing for the more homogeneous subgroups is determined; the dosing results are expressed as a fraction of the clinician's usual heterogeneous whole group dosages.

For any one specific polymorphic DME (assuming all other relevant polymorphic DME have normal activity), the usual drug dose seen in a population is the weighted summation of the drug dosages in each genetic different subpopulation expressed in equation 1: (See Kirchheiner Acta Psychiatr Scand 2001:104: 173-192 BUT note authors made mistake in non-numbered equation between Equations 1 and 2, page 178):

$$D_{pop}=f_{EM}*D_{EM}+f_{IM}*D_{IM}+f_{PM}*D_{PM} \quad \text{(Equation 1)}$$

Assuming the goal is to maintain the same AUC for all three subpopulations of patients, the following subpopulation dosing relationships hold:

$$D_{PM}=D_{EM}*(AUC_{EM}/AUC_{PM}) \text{ OR } D_{PM}=D_{EM}*R \text{ if } R=(AUC_{EM}/AUC_{PM}) \quad \text{(Equation 2)}$$

$$D_{IM}=D_{EM}*(AUC_{EM}/AUC_{IM}) \text{ OR } D_{IM}=D_{EM}*S \text{ if } S=(AUC_{EM}/AUC_{IM}) \quad \text{(Equation 3)}$$

By substituting equations 2 and 3 into equation 1, and then rearranging the equation to solve for the percent dose adjustment needed for each subgroup relative to the population dose:

$$D_{EM}(\%)=100/(f_{EM}+f_{IM}*S+f_{PM}*R) \quad \text{(Equation 4)}$$

$$D_{PM}(\%)=R*D_{EM} \quad \text{(Equation 5)}$$

$$D_{IM}(\%)=S*D_{EM} \quad \text{(Equation 6)}$$

Equations 4, 5, and 6 show how the dosing for the more homogeneous subgroups is determined and how the dosing results are expressed as a fraction of the clinician's usual heterogeneous whole group dosages.

Determining "Minimal Dose Adjustment Units"

The cumulative effect of various genetic or environmentally based alterations in DME activity will result in interpatient variability in subsequent drug dosing requirements. If the variability is large enough, then "one size fits all" dosing approach can cause noticeable toxicity in some patients and lack of efficacy in others. In this situation, clinicians alter their drug prescribing or drug dosing behavior. We define the smallest clinically relevant dosing change used by clinicians to compensate for this interpatient variability as the "minimal dose adjustment unit" (MDA unit).

The MDA unit for neuropsychiatric drugs is 20%. This means that a clinician will alter their dosing of neuropsychiatric medications in response to specific information if the dosing change is 20% or greater. Perturbations that either singly or in combination suggest a <20% change in dosing of neuropsychiatric medications are usually ignored.

MDA units are additive—so that a patient with one MDA unit from a genetic polymorphism and one MDA unit from a drug interaction needs a 40% reduction in dose.

Example: The approach in the previous section leads to individualized initial drug dose recommendations for each of the 3 subgroups (extensive, poor and intermediate metabolizers). Each subgroup represents a specific number of functional alleles for the specific DME (extensive metabolizers have 2 functional, intermediate metabolizers have 1 functional and poor metabolizers have 0 functional). The resultant dosing recommendations are expressed as percentages of the clinician's usual starting dose. It is possible to investigate the effect of increasing numbers of non-functional alleles using these new dosing recommendations. For example, if $DR_X\%$ is the dosing recommendation for subgroup X expressed as a percentage of the clinician's usual starting dose then the following are true:

Effect of claim 1 non-functional allele= $(DR_{EM}\%-DR_{IM}\%)/DR_{EM}\%$

Effect of 2 non-functional allele=$(DR_{EM}\%-DR_{PM}\%)/DR_{EM}\%$

Below is a spreadsheet (Table 3) that examines this for CYP2D6, CYP2C19 and CYP2C9. The summary table below demonstrates:

a. it is apparent that each additional nonfunctional allele alters dosing recommendation by at least 20%
b. there is a "genetic dose"—"dosing reduction" relationship that appears constant across these 3 CYP450 genes. This approach can be used to solidify the importance of subsequent DM genes and to quantify their effect in MDA units.
c. 2D6 and 2C19 have 1 MDA unit per non-functional allele
d. 2C9 has 2 MDA units per non-functional allele. This implies that drug metabolized through 2C9 have very large variability in dosage requirements. This confirms the clinical impression about these drugs (warfarin, phenytoin).

TABLE 3

| 2D6 | | 2D6 | PM (%) | IM (%) | EM (%) | UM (%) | | 2 al | 1 al | 2 al/ 1 al |
|---|---|---|---|---|---|---|---|---|---|---|
| Antipsychotics | A | atomoxetine | 20 | 100 | 100 | 100 | | 0.80 | 0.00 | |
| Psychostimulant | B | imipramine | 28 | 79 | 131 | 182 | | 0.79 | 0.40 | 1.98 |
| Antidepressants | A | perphenazine | 31 | 80 | 129 | 178 | | 0.76 | 0.38 | 2.00 |
| Antidepressants - TCA | B | doxepin | 36 | 82 | 127 | 173 | | 0.72 | 0.35 | 2.02 |
| Antipsychotics | B | maprotiline | 36 | 82 | 127 | 173 | | 0.72 | 0.35 | 2.02 |
| Antipsychotics | B | trimipramine | 37 | 91 | 131 | 178 | | 0.72 | 0.31 | 2.35 |
| Antipsychotics | A | thioridazine | 40 | 85 | 126 | 140 | | 0.68 | 0.33 | 2.10 |
| Antidepressants | A | desipramine | 42 | 83 | 125 | 167 | | 0.66 | 0.34 | 1.98 |
| Antidepressants | A | nortriptyline | 53 | 96 | 119 | 152 | | 0.55 | 0.19 | 2.87 |
| Antidepressants - TCA | B | clomipramine | 60 | 89 | 117 | 146 | | 0.49 | 0.24 | 2.04 |
| Antipsychotics | A | olanzapine | 61 | 105 | 122 | 139 | | 0.50 | 0.14 | 3.59 |
| Antidepressants - SSRIs | A | zuclopenthixol | 63 | 90 | 116 | 142 | | 0.46 | 0.22 | 2.04 |
| Antipsychotics | A | paroxetine | 66 | 90 | 114 | 138 | | 0.42 | 0.21 | 2.00 |
| Antipsychotics | A | venlafaxine | 68 | 86 | 109 | 130 | | 0.38 | 0.21 | 1.78 |
| Antipsychotics | B | fluvoxamine | 69 | 93 | 112 | 131 | | 0.38 | 0.17 | 2.26 |
| Antipsychotics | A | aripiprazole | 70 | 92 | 113 | 134 | | 0.38 | 0.19 | 2.05 |
| Antipsychotics | B | amitryptiline | 73 | 92 | 111 | 130 | | 0.34 | 0.17 | 2.00 |
| Antidepressants | A | flupentixol | 74 | 86 | 116 | 146 | | 0.36 | 0.26 | 1.40 |
| Antidepressants | B | mianserin | 74 | 90 | 114 | 134 | | 0.35 | 0.21 | 1.67 |
| Antipsychotics | A | haloperidol | 76 | 97 | 107 | 126 | | 0.29 | 0.09 | 3.10 |
| Antidepressants - TCA | A | trazadone | 76 | 93 | 110 | 127 | | 0.31 | 0.15 | 2.00 |
| Antidepressants - SSRIs | B | fluoxetine | 78 | 94 | 107 | 120 | | 0.27 | 0.12 | 2.23 |
| Antidepressants - TCA | A | perazine | 86 | 91 | 110 | 117 | | 0.22 | 0.17 | 1.26 |
| Antipsychotics | A | risperidone | 87 | 96 | 106 | 116 | | 0.18 | 0.09 | 1.90 |
| Antidepressants - TCA | A | buproprion | 90 | 97 | 104 | 111 | | 0.13 | 0.07 | 2.00 |
| Antidepressants - SSRIs | A | nefazodone | 90 | 97 | 105 | 113 | | 0.14 | 0.08 | 1.88 |
| | | | | | | | Count | 26 | 26 | 25 |
| | | | | | | | Average | 0.45 | 0.22 | 2.10 |
| | | | | | | | St. Dev. | 0.20 | 0.10 | 0.48 |
| Antidepressants - SSRIs | A | pimozide | 95 | 99 | 102 | 105 | | 0.07 | 0.03 | |
| Antidepressants - TCA | B | citalopram | 98 | 100 | 101 | 102 | | 0.03 | 0.01 | |
| Antidepressants | B | sertraline | 99 | 100 | 100 | 100 | | 0.01 | 0.00 | |
| Antidepressants | A | levomepromazine | 100 | 100 | 100 | 100 | | 0.00 | 0.00 | |
| Antidepressants | A | mirtazapine | 102 | 101 | 99 | 97 | | −0.03 | −0.02 | |
| Antidepressants - SSRIs | B | clozapine | 113 | 104 | 94 | 84 | | −0.20 | −0.11 | |
| Antidepressants - TCA | B | moclobemide | 121 | 107 | 92 | 77 | | −0.32 | −0.16 | |

| | | PM (%) | IM (%) | UM (%) | | 2 al | 1 al | 2 al/ 1 al |
|---|---|---|---|---|---|---|---|---|
| | 2C19 | | | | | | | |
| Antidepressants - TCA | trimipramine | 45 | 62 | 111 | | 0.59 | 0.53 | 1.12 |
| Antidepressants - TCA | doxepin | 46 | 91 | 105 | | 0.54 | 0.13 | 4.07 |
| Antidepressants - TCA | amitryptiline | 53 | 81 | 109 | | 0.51 | 0.26 | 2.00 |
| Antidepressants | moclobemide | 54 | 82 | 110 | | 0.51 | 0.25 | 2.00 |
| Antidepressants - TCA | imipramine | 58 | 83 | 108 | | 0.46 | 0.23 | 2.00 |
| Antidepressants - SSRIs | citalopram | 61 | 84 | 108 | | 0.44 | 0.22 | 1.96 |
| Antidepressants - TCA | clomipramine | 62 | 79 | 110 | | 0.44 | 0.28 | 1.55 |
| Antidepressants - SSRIs | fluoxetine | 70 | 86 | 107 | | 0.35 | 0.20 | 1.76 |
| Antidepressants - SSRIs | sertraline | 75 | 90 | 105 | | 0.29 | 0.14 | 2.00 |
| Antipsychotics | clozapine | 78 | 91 | 104 | | 0.25 | 0.13 | 2.00 |
| Antipsychotics | zotepine | 82 | 83 | 104 | | 0.21 | 0.11 | 2.00 |
| Antidepressants - SSRIs | fluvoxamine | 93 | 97 | 101 | | 0.08 | 0.04 | 2.00 |
| | | | | | Count | 12 | 12 | 12 |
| | | | | | Average | 0.39 | 0.21 | 2.04 |
| | | | | | St. Dev. | 0.16 | 0.12 | 0.69 |
| Antidepressants | maprotiline | 100 | 100 | 100 | | 0.00 | 0.00 | |
| Antidepressants | mianserin | 100 | 100 | 100 | | 0.00 | 0.00 | |
| | 2C9 | | | | | | | |
| Antidiabetic Agent, Sulfonylurea | Amaryl | 20% | 70% | 120% | | 0.83 | 0.42 | 2.00 |
| Antidiabetic Agent, Solfonylurea | Glucotrol, Glipizide | 20% | 70% | 120% | | 0.83 | 0.42 | 2.00 |
| Antidiabetic Agent, Sulfonylurea | DiaBeta, Glucovance | 20% | 70% | 120% | | 0.83 | 0.42 | 2.00 |
| Angiotensin II Receptor Antagonist | Cozaar, Hyzaar | 20% | 50% | 100% | | 0.80 | 0.50 | 1.60 |
| Antidiabetic Agent, Sulfonylurea | Diabinese, Orinase, Tolinase | 20% | 60% | 120% | | 0.83 | 0.58 | 1.43 |
| Anticoagulant | Coumadin | 20% | 50% | 130% | | 0.85 | 0.62 | 1.38 |
| Analgesic - NSAID | Celebrex | 35% | 70% | 100% | | 0.65 | 0.30 | 2.17 |
| Antilipemic | Lescol | 35% | 80% | 100% | | 0.65 | 0.20 | 3.25 |
| Anticonvulsant | Dilantin | 40% | 70% | 110% | | 0.64 | 0.36 | 1.75 |

TABLE 3-continued

|  |  |  | Count | 9 | 9 | 9 |
|---|---|---|---|---|---|---|
|  |  |  | Average | 0.77 | 0.42 | 1.95 |
|  |  |  | St Dev. | 0.09 | 0.13 | 0.56 |
| 20 | 50 | 120 |  | 0.83 | 0.58 | 1.43 |
| 20 | 50 | 100 |  | 0.80 | 0.50 | 1.60 |

TABLE 4

Relationship between non-functional alleles and dose reduction

| Gene | Average percentage dose reduction if 1 non-functional allele | Average percentage dose reduction if 2 non-functional allele | Effect on percentage dose reduction of 2 non-functional alleles compared to 1 |
|---|---|---|---|
| 2D6 | 22% ± 10% (n = 26) | 45% ± 20% (n = 26) | 2.10 ± 0.48% (n = 25) |
| 2C19 | 21% ± 12% (n = 12) | 39% ± 16% (n = 12) | 2.04 ± 0.69 (n = 12) |
| 2C9 | 42% ± 13% (n = 9) | 77% ± 9% (n = 9) | 1.95 ± 0.56 (n = 9) |

Determining Final Dosage Requirements

For some drugs, there is very little pharmacokinetic genetic variability but rather clinically relevant pharmacodynamic genetic variability most likely at the drug's receptor. For these medications, the impact of genetic testing will be reflected in the final dosage requirements instead of the initial dosage requirements.

Studies that demonstrate this genetic-pharmacodynamic effect will be captured in the software that encodes the calculations used to derive the simplicity index described earlier. This invention will incorporate this information and report not only the rank simplicity index of the potential drug candidates but also those candidates that would require a higher than expected dosing requirement to achieve the desire effect.

Population Models

The purpose of population pharmacokinetic modeling is to describe the statistical distribution of pharmacokinetic parameters in the population under study and to identify potential sources of intra- and inter-individual variability among patients. Population modeling is a powerful tool to study if, and to what extent, demographic parameters (e.g. age, weight, and gender), pathophysiologic conditions (e.g. as reflected by creatinine clearance) and pharmacogenetic variability can influence the dose-concentration relationship. A population pharmacokinetic analysis is robust, can handle sparse data (such as therapeutic drug monitoring data) and is designed to generate a full description of the drug's PK behavior in the population. A "population model" of the invention provides a description of the statistical distribution of at least one pharmacokinetic parameter in a given population and identifies at least on potential source of variability among patients with regards to a particular compound or agent. A population model of the invention may further provide mean parameter estimates with their dispersion, between subject variability and residual variability, within subject variability, model misspecification and measurement error for a particular compound.

An embodiment of the invention provides several novel population models for predicting a medication concentration-time profile and for selecting a dosing regimen based on a user-entered target range (see examples). The computerized methods and/or computer-assisted methods (including software algorithms) of the invention employ population models such as, but not limited to, the novel population models of the invention and externally developed population models. In an embodiment, such externally developed population models are adjusted or rearranged in such a manner that they can be programmed into the software of the invention.

In various embodiments, the computerized methods and/or computer-assisted methods (including software algorithms) of the invention comprise the step of monitoring a biomarker. By "biomarker" is intended any molecule or species present in a patient that is indicative of the concentration or specific activity of an exogenous compound in the subject. Biomarkers include, but are not limited to, a compound, a metabolite of the compound, an active metabolite of the compound, a molecule induced or altered by administration of the compound of interest, and a molecule that exhibits an altered cytological, cellular, or subcellular location concentration profile in after exposure to a compound of interest. Methods of monitoring biomarkers are known in the art and include, but are not limited to, therapeutic drug monitoring. Any method of monitoring a biomarker suitable for the indicated biomarker known in the art is useful in the practice of the invention.

Exemplary computerized methods and/or computer-assisted methods (including software algorithms) of the invention use data generated by therapeutic drug monitoring (TDM). TDM is the process of measuring one or more concentrations of a given drug or its active metabolite(s) in biological sample such as, but not limited to, blood (or in plasma or serum) with the purpose to optimize the patient's dosing regimen. The invention encompasses any means of measuring one or more concentrations of a given drug or its active metabolite(s) in a biological sample known in the art. By "biological sample" is intended a sample collected from a subject including, but not limited to, tissues, cells, mucosa, fluid, scrapings, hairs, cell lysates, blood, plasma, serum, and secretions. Biological samples such as blood samples can be obtained by any method known to one skilled in the art.

The following examples are offered by way of illustration and not limitation.

EXPERIMENTAL

Example 1

Optimization of Compound Dosage in an Autistic Patient

An 11-year-old boy with autism was started on risperidone (Risperdal®) therapy, at 0.5 mg two times a day. The patient's pressured speech and labile mood did not improve with time. The lack of efficacy could be due to insufficient coverage or to non-compliance. The patient's dosing regimen was analyzed by the methods of this invention.

Step 1 Dose Appropriateness Analysis.

The patient demographic data (age, sex, weight) and the risperidone dose and times of administration were entered into the program. A population model was selected. The population model selected was a Risperidone model based on data of pediatric psychiatry patients. As risperidone is metabolized by CYP2D6, there are 3 models: one for extensive metabolizers (EM model), one for intermediate metabolizers (IM model) and one for poor metabolizers (PM model).

Figure 2A:
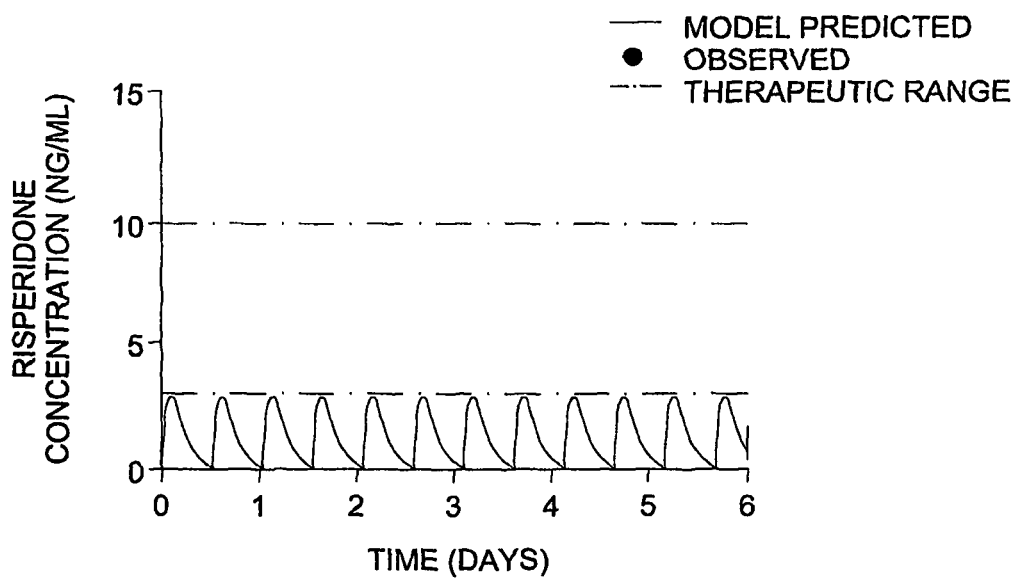
FIG. 2 presents risperidone pharmacokinetic profiles for three different dosing regimens for a particular patient. Panel A depicts an exemplary pharmacokinetic model-based simulation of the risperidone concentration time profile. Panel B depicts an exemplary pharmacokinetic model-based simulation of the risperidone concentration time profile after altering the dosing regimen. Panel C depicts an exemplary pharmacokinetic model-based simulation of the risperidone concentration time profile with a third dosing regimen. In each panel a solid line indicates the patient's compound concentration predicted by the methods of the invention in each dosing regimen and the broken line indicates the therapeutic range, in this example arbitrarily chosen to be between 3 and 10 ng/mL. The observed biomarker value is indicated with solid circles or triangles.

The genotype of the patient was determined and found to be CYP2D6 *1/*1. This genotype fit the extensive metabolizer (EM model). The patient's data and the genotype were analyzed by an algorithm of the invention and a drug concentration profile for the patient was generated. An exemplary pharmacokinetic model-based simulation of the risperidone concentration time profile based on this patient's data is shown in FIG. 2a. The average concentration was predicted to be around ~2 ng/mL. This information is integrated with a target drug concentration profile or therapeutic value. The therapeutic value for risperidone ranges between 3 and 10 ng/mL. Comparison of the drug concentration profile for the patient and the target drug concentration profile indicated that if the patient were adherent, the dose may be too low. The algorithm generated two recommendations: the dose can be increased and a biomarker should be monitored.

Step 2. Integration of Biomarker Evaluation in Recommended Dosage Regimen

Figure 2B:
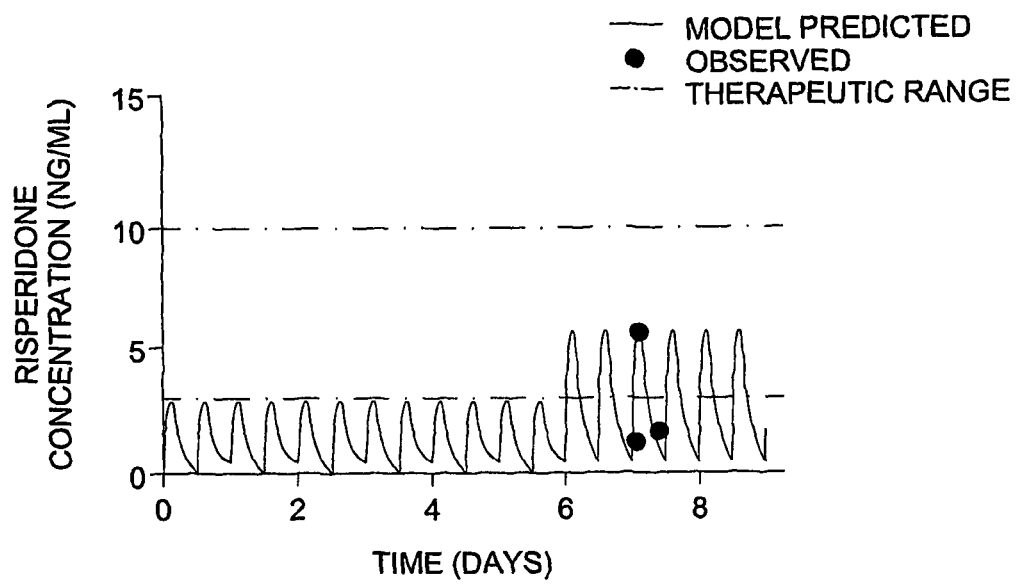
Figure 2C:
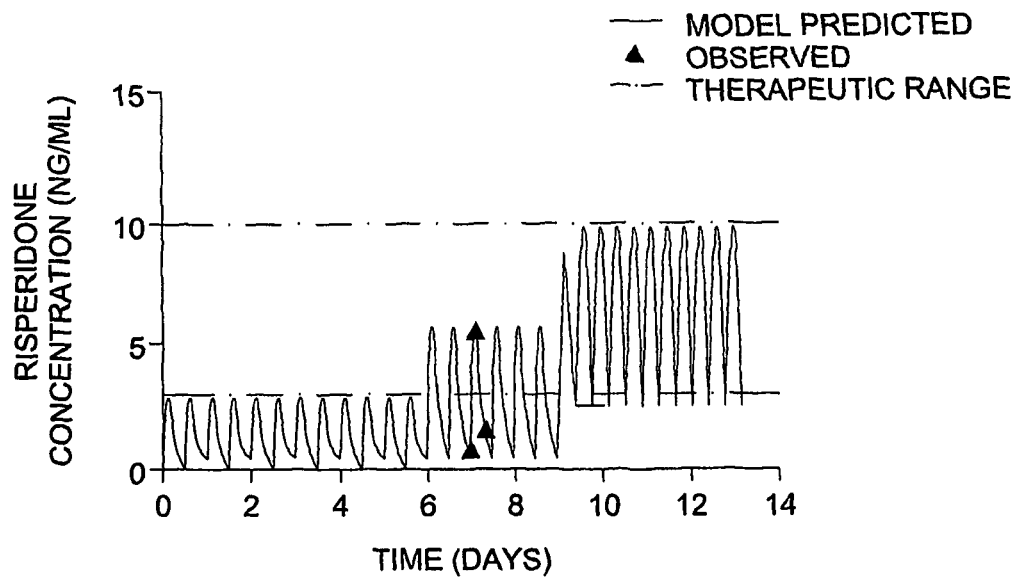

The risperidone dose was increased to 1 mg given twice a day (morning and evening). In addition, a biomarker evaluation was performed. Drug levels were ordered and therapeutic drug monitoring were performed. The pre-dose level and two post dose levels (1 h after dose) and (4 h after dose) were measured. These data were entered in the software program. The software program performed a Bayesian recalculation based on the a priori information from the model in combination with the new patient specific information (i.e. the drug levels). Exemplary results of this Bayesian update are shown in FIG. 2b. The concentrations were not within the target range for the major part of the dosing interval. Depending on patient's response this would allow for further increasing the dose. The pharmacokinetic simulation also indicated that this patient has a rather rapid elimination of the drug form the body. The software program generated several recommendations. In order to maintain the target concentration more frequent dosing has to be considered. Based on the Bayes pharmacokinetic estimates for this patient and given the chosen target range the dosing regimen that best meets the criteria would be 1.5 mg dosed every 8 hours. An exemplary model-based profile and subsequent Bayesian individualization process are shown in FIG. 2c.

The above-described methods according the present invention can be implemented on a computer system such as a personal computer, a client/server system, a local area network, or the like. The computer system may be portable including but not limited to a laptop computer or hand-held computer. Further the computer may be a general purpose system capable of executing a variety of commercially available software products, or may be designed specifically to run only the drug identification and selection algorithms that are the subject of this invention. The computer system may include a display unit, a main processing unit, and one or more input/output devices. The one or more input/output device may include a touchscreen, a keyboard, a mouse, and a printer. The device may include a variety of external communication interfaces such as universal serial bus (USB), wireless, including but not limited to infrared and RF protocols, serial ports and parallel ports. The display unit may be any typical display device, such as a cathode-ray tube, liquid crystal display, or the like.

The main processing unit may further include essential processing unit (CPU) in memory, and a persistent storage device that are interconnected together. The CPU may control the operation of the computer and may execute one or more software applications that implement the steps of an embodiment of the present invention. The software applications may be stored permanently in the persistent storage device that stores the software applications even when the power is off and then loaded into the memory when the CPU is ready to execute the particular software application. The persistent storage device may be a hard disk drive, an optimal drive, a tape drive or the like. The memory may include a random access memory (RAM), a read only memory (ROM), or the like.

Exemplary Simplicity Index Software Tool

As introduced above an algorithm used to construct the drug predictive index ("simplicity index") utilizes an initial identification of the disease phenotype (e.g. epilepsy, depression, etc.), which provides a preliminary identification of the universe of possible medications for that condition. An exemplary software tool for producing the simplicity index uses linear algebra computational science to integrate disease specific evidence based medicine data, drug specific basic pharmacology characteristics, patient specific advanced pharmacology principles, and patient specific environmental and genetic factors to produce a ranking of potential medications for an individual patient based on these factors. There are separate algorithms for each disease phenotype but the algorithms can be run simultaneously. Further, in the exemplary embodiment, there are three components used to produce the final ranking score: a disease matrix, a patient vector and a weighting vector. Each of the five factors and three components will be defined below followed by an example with a sample output. The output contains both the drug predictive index and an adherence score.

Definitions:

Disease Specific Evidence Based Medicine Data

Disease specific evidence based medicine data consists of disease specific efficacy and tolerability data for potentially effective medications. This disease specific efficacy and tolerability data may exist for age or disease subgroups; each age or disease subgroup is considered separately. For example in epilepsy, evidence based data exists for five age groups (neonates, infants, children, adults, and elderly adults) along with four disease subgroups (partial onset seizures, generalized tonic clonic seizures, absence seizures, and myoclonic seizures). In this example, there would be a maximum of 20 separate evidence based data sets covering all age-seizure type combinations.

The first step in the evidence based approach is to identify all relevant scientific information about the efficacy and tolerability of any potential therapeutic modality (medical, surgical or dietary). Articles are identified through multiple methods including, but not limited to, electronic literature searches of the medical literature, hand searches of major medical journals, the Cochrane library of randomized controlled trials, and the reference lists of all studies identified from the electronic literature searches. These articles may include, but are not limited to, randomized control trials, nonrandomized controlled trials, case series, case reports, and expert opinions. Supplementary data is found in package inserts of individual drugs.

The data in each article is evaluated for drug specific efficacy and tolerability data. The analysis is performed using the grading system used by the national scientific organization associated with that specialty. If there is no national scientific organization associated with the specialty then the default grading system is the American Academy of Neurology evaluation system. After the evidence based analysis is complete, the efficacy and tolerability data for each potential drug (stratified by age and disease subgroup) is summarized according to the following Table 5 using a scale from 1+ to −1.

TABLE 5

Drug scoring system for efficacy and tolerability data

| Efficacy or Tolerability score | Type of data (shown for efficacy only) |
| --- | --- |
| 1.0 | FDA indication for condition |
| 0.9 | Evidence Based Guideline Level A recommendation |
| 0.9 | Meta-analysis evidence of efficacy |
| 0.7 | Evidence Based Guideline Level B recommendation |
| 0.7 | RCT evidence better efficacy than another drug or placebo |
| 0.3 | Evidence Based Guideline Level C recommendation |
| 0.3 | non RCT clinical trial evidence of efficacy |
| 0.3 | Expert opinion - drug is efficacious |
| 0.0 | No data |
| −0.3 | Expert opinion - evidence of worsening |
| −0.3 | non RCT clinical trial evidence of worsening |
| −0.7 | RCT evidence worse efficacy than another drug or placebo |
| −0.9 | Meta-analysis evidence of lack of efficacy or worsening |
| −0.9 | Evidence Based Guideline evidence of lack of efficacy or worsen |
| −1.0 | FDA contraindication for condition |

Drug Specific Basic Pharmacology Characteristics

Drug specific basic pharmacology characteristics are evaluated in three categories: Preclinical toxicity, fundamental clinical pharmacokinetic variables and drug safety. An example in the preclinical toxicity category is a drug's therapeutic index. This is defined as the ratio of LD50/TD50 where TD50 is the dose of the medication that results in 50% of the animals tested achieving the desired therapeutic outcome while LD50 is the dose of the medication that results in 50% of the animals tested dying. Fundamental clinical pharmacokinetic variables include, but are not limited to, i) a drug's bioavailability (fraction of the dose which reaches the systemic circulation as intact drug), ii) the fraction of the drug circulating unbound (defined by the extent to which a drug is bound in plasma or blood= [unbound drug concentration]/[total drug concentration]), iii) the type of metabolism the drug undergoes (whether linear or non-linear), iv) the type of elimination the drug undergoes (e.g. percentage of drug renally excreted or hepatically metabolized) and v) the drug's half-life.

Drug safety includes, but is not limited to, the risk of life threatening side effects (idiosyncratic reactions) and the risk of teratogenicity. For each drug under consideration, each variable in the three categories is scored on a scale from +1 (most favorable) to −1 (most unfavorable).

Patient Specific Advanced Pharmacology Factors

Patient specific advanced pharmacology factors include i) bidirectional pharmacokinetic or pharmacodynamic drug-drug interactions and ii) bidirectional pharmacodynamic drug-disease interactions. A pharmacokinetic drug-drug interaction is considered potentially clinically significant if there is a documented interaction that shows one drug either induces or inhibits the activity of a specific enzyme associated with the metabolism of the other drug by ≥20%. Only concomitant medications actually being taken at the time of the analysis are considered in the analysis. For drug-disease interactions, the word "diseases" refers to all forms of altered health ranging from single organ dysfunction (e.g. renal failure) to whole body illness (e.g. systemic lupus erythematosus). The potential for drug-drug or drug-disease interactions is evaluated on a scale from +1 (most favorable) to −1 (most unfavorable).

To clarify using an example: In a specific patient, assume drug A is being evaluated for use in disease D. The patient is currently taking oral contraceptives, a statin for hypercholesterolemia and is overweight. To evaluate the "Patient specific advanced pharmacology factors" for drug A for this patient there are 8 potential drug-drug interactions and 4 potential drug-disease interactions to evaluate: i) pharmacokinetic effect of drug A on oral contraceptives, ii) pharmacokinetic effect of oral contraceptives on drug A, iii) pharmacokinetic effect of drug A on statin medications, iv) pharmacokinetic effect of statin medication on drug A, v)-viii) the same four combinations mentioned previously but examining the pharmacodynamic interactions between drugs, ix) pharmacodynamic effect of drug A on hypercholesterolemia, x) pharmacodynamic effect of hypercholesterolemia on drug A, xi) pharmacodynamic effect of drug A on weight, xii) pharmacodynamic effect of weight on drug A. If Drug A has i) a clinically significant negative effect on statin pharmacokinetics and ii) causes weight gain then Drug A would receive a score of −1 for these two assessments and a score of 0 for the remaining 10 evaluations. This approach is repeated for each drug under consideration (e.g. drugs B, C, . . . etc).

Patient Specific Environmental Factors

Patient specific environmental factors involve unidirectional, pharmacokinetic or pharmacodynamic, drug-environment interactions. Unidirectional refers to the effect of the environmental agent on the drug. A pharmacokinetic drug-environment interaction is considered potentially clinically significant if there is a documented interaction that shows the environmental agent either induces or inhibits the activity of a specific enzyme associated with the metabolism of the drug by ≥20%. A pharmacodynamic drug-environment interaction is considered potentially clinically significant if there is a documented interaction that shows the environmental factor alters (either positively or negatively) the action of the drug by ≥20%. Only environmental factors occurring at the time of the analysis are considered in the analysis. For drug-environment interactions, the word "environment" refers to all forms of exposure ranging from food (grapefruit juice) to herbal/vitamin supplements (e.g. St. Johns wort) to voluntary toxic exposures (e.g. smoking or alcohol) to involuntary toxic exposures (second hand smoke, pesticides). The potential for drug environment interactions is evaluated on a scale from +1 (most favorable) to −1 (most unfavorable).

Patient Specific Genetic Factors

Patient specific genetic factors involve unidirectional, pharmacokinetic or pharmacodynamic, drug-gene interactions. Unidirectional refers to the effect of the genetic variation on the pharmacokinetic or pharmacodynamic action of the drug. A pharmacokinetic drug-gene interaction is considered potentially clinically significant if there is a documented interaction that shows the genetic factor either increases or reduces the activity of a specific enzyme associated with the metabolism of the drug by ≥20%. A pharmacodynamic drug-gene interaction is considered potentially clinically significant if there is a documented interaction that shows the genetic factor alters (either positively or negatively) the action of the drug by ≥20%. For drug-gene interactions, the word "gene" refers to all forms of genetic variability including DNA variability, mRNA variability, protein alterations or metabolite alterations. The potential for drug-gene interactions is evaluated on a scale from +1 (most favorable) to −1 (most unfavorable).

Disease Matrix

An example (very small) segment of a disease matrix is provided in FIG. 3. The disease matrix includes column headings for distinct treatment modalities (e.g. medication, therapy, surgery, dietary plan, etc.) while the rows are distinct factors from the five categories listed above: disease specific evidence based medicine data, drug specific basic pharmacology characteristics, patient specific advanced pharmacology principles, patient specific environmental and patient specific genetic factors. The value in each cell in the matrix ranges from +1 (favorable quality/result) to −1 (unfavorable quality/result).

Referring to the example disease matrix segment in FIG. 3, the first column 10 lists the specific factor to be evaluated for a list of specific treatments and/or drugs; column 12 provides the category for the specific factor; and columns 14-20 provide the specific disease matrix values that the specific factor associates with a specific drug or treatment. For example, the factor of Row 8, "Pharmacokinetics (metabolism)," is listed in the "Basic pharmacology" category and has a wide variance of matrix values or scores depending upon the proposed drug or treatment: carbamazepine has a −0.5 matrix value; phenobarbital has a 1.0 matrix value; phenytoin has a −1.0 matrix value; and topiramate has a 1.0 matrix value. As another example, the factor of Row 23, "Patient is a CYP2C9 poor metabolizer," is listed in the "Genetic factors" category and also has a variance of matrix scores depending upon the proposed drug or treatment: carbamazepine has a −0.3 matrix value; phenobarbital has a −1.0 matrix value; phenytoin has a −1.0 matrix value; and topiramate has a 0.0 matrix value.

Patient Vector Column (Matrix)

A patient vector is constructed for each individual patient. In the exemplary embodiment, the patient vector is a column (not shown in FIG. 3) of the disease matrix. Optionally, the patient vector may be a 1 by N matrix, where N is the number of distinct factors for that particular disease algorithm taken from the five categories listed above: disease specific evidence based medicine data, drug specific basic pharmacology characteristics, patient specific advanced pharmacology principles, patient specific environmental and patient specific genetic factors. The items in the patient vector are determined by the response to a series of YES/NO/UNKNOWN questions for each of the variables considered. The questions are yes/no questions and the matrix enters a 0 (for no), 0.5 (for unknown) or a 1 (for yes).

Weighting Vector

A weighting vector is constructed for each disease matrix. In the exemplary embodiment, the weighting vector is a column (not shown in FIG. 3) of the disease matrix. Optionally, the weighting vector is a 1 by N matrix, where N is the number of distinct factors for that particular disease algorithm taken from the five categories listed above: disease specific evidence based medicine data, drug specific basic pharmacology characteristics, patient specific advanced pharmacology principles, patient specific environmental and patient specific genetic factors. The values in the weighting vector are determined by either a supervised system (e.g. expert system) or an unsupervised system (e.g. neural network or an artificial intelligence system). The weighting is usually different for the different factors in the disease algorithm. For example, referring back to FIG. 3, Row 2, "Child with partial seizures starting therapy" has a weight of claim 1000, Row 13, "The patient has migraines/headaches" has a weight of claim 150, and Row 23, "Patient is a CYP2C9 poor metabolizer" has a weight of 250.

Algorithm Output

The main output of the algorithm is a ranking of all potential therapies (medications, surgeries or diet) for that specific disease ranging from most likely to be successful (highest score) to least likely to be successful (lowest score). Each drug's score is the product of the patient vector, the weighting vector and the particular drug's column value in the disease matrix. The dosing for the drug is determined by the algorithm described above. In the exemplary embodiment, the output display includes the top 5 factors contributing and the lowest 3 factor detracting from the score are included for evaluation. Above the ranking is an adherence score reflecting the likelihood the patient will adhere to the proposed treatment regimen. The determination and interpretation of this number is described in the Adherence score section.

Adherence Score

The adherence score is determined in a similar fashion to the simplicity index: the score is the product of an "adherence matrix", a patient vector and a weighting vector. For each disease, potential adherence problems are assessed using a series of approximately 10 yes/no/unknown questions. If all questions are answered unknown then the adherence score will be 50% implying a 50% chance the patient will adhere to the treatment regimens. The more questions that are answered "no", the higher the adherence score and the greater the chance the patient will adhere to the prescribed treatment regimen. The more questions answered "yes", the lower the adherence score and the greater the chance the patient will not adhere to the prescribed treatment regimen.

Figure 4:
FIG. 4 is a screen shot illustrating a step of an exemplary computer implemented method of the present invention.

Patient Example:
  History: The patient is a 7 year old male presenting with frequent staring episodes lasting 30-60 seconds associated with unresponsiveness, facial twitching and extreme tiredness afterwards. He develops a funny taste in his mouth in the few minutes before the events occur. He has had about 10 of these in the past year with 3 in the last month. The patient does not have depression, ADHD or anxiety but does have frequent migraines. The patient is currently taking erythromycin for an infection but takes no chronic medications. There is no family history of epilepsy. The patient loves to drink grapefruit juice. The family has insurance, no transportation problems and no identifiable stressors.
  Physical examination: Normal in detail except the patient is very overweight
  Lab tests: EEG shows normal background and focal discharges in the temporal lobe. MRI of the brain is normal. Pharmacogenetic testing shows a CYP2C9 polymorphism that makes him a poor metabolism for drugs metabolized by CYP2C9.
  Diagnosis: Newly diagnosed idiopathic partial epilepsy characterized by partial onset seizures.
  Need: Determine the best antiepileptic medications for this specific patient.
  Step 1: As can be seen if FIG. 4, after logging onto algorithm program—select disease—a screen will be provided in which the physician will select in field 22 that the patient's diagnosis is Epilepsy, but in field 24 that the patient's diagnosis is not depression.

Figure 5:
FIG. 5 is a screen shot illustrating another step of an exemplary computer implemented method of the present invention.

Step 2: As can be seen if FIG. 5, a next step—enter age, gender and puberty status—another screen will be provided in which the physician selects in field 26 that the patient is between 2 and 18 years old, in field 28 that the patient is male and in field 30 that the patient is pre-pubertal.

Figure 6:
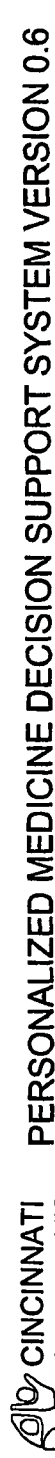
FIG. 6 is a screen shot illustrating another step of an exemplary computer implemented method of the present invention.

Step 3: As can be seen in FIG. 6, a next step—select type of epilepsy and whether starting or on medications—another screen will be provided in which the physician selects in field 32 that the patient is a child with partial seizures and no previous treatment. Fields 34-50 are not selected.

Figure 7:
FIG. 7 is a screen shot illustrating another step of an exemplary computer implemented method of the present invention.

Step 4: As can be seen in FIG. 7, a next step—enter comorbid conditions—another screen will be provided in which the physician selects in field 52 that the patient is overweight and in field 54 that the patient has migraines or headaches. Fields 56-62 are not selected.

Figure 8:
FIG. 8 is a screen shot illustrating another step of an exemplary computer implemented method of the present invention.

Step 5: As can be seen in FIG. 8, a next step—enter EEG and MRI test results—another screen will be provided in which the physician selects in field 64 that the patient's EEG is abnormal with epileptiform discharges and in field 66 that the patient's MRI/CT shows normal cortical structure.

Figure 9:
FIG. 9 is a screen shot illustrating another step of an exemplary computer implemented method of the present invention.

Step 6: As can be seen in FIG. 9, a next step—enter concomitant medications—another screen will be provided in which the physician selects in field 68 that the patient is taking an antibiotic, antiviral, antifungal, antiparasitic or anti-TB medications. Fields 70-88 are not selected.

Figure 10:
FIG. 10 is a screen shot illustrating another step of an exemplary computer implemented method of the present invention.

Step 7: As can be seen in FIG. 10, a next step—the enter concomitant medications step is continued and another screen will be provided for the physician to identify specific antibiotic, antiviral, antifungal, antiparasitic or anti-TB medications that the patient is taking. In this example, the physician selects in field 104 that the patient is taking erythromycin. Fields 90-102 and 106-114 are not selected.

Figure 11:
FIG. 11 is a screen shot illustrating another step of an exemplary computer implemented method of the present invention.

Step 8: As can be seen in FIG. 11, a next step—enter environmental factors—another screen will be provided in which the physician selects in field 118 that the patient drinks grapefruit juice. Fields 116 and 120-120 are not selected since the patient does not smoke or drink alcohol or green tea.

Figure 12:
FIG. 12 is a screen shot illustrating another step of an exemplary computer implemented method of the present invention.

Step 9: As can be seen in FIG. 12, a next step—enter genetic factors—another screen will be provided in which the physician selects in field 126 that the patient CYP2C9 poor metabolism. As will be appreciated by those of ordinary skill, such genetic data may also be entered automatically with the assistance of the system that analyzes the patient's genetic data.

Step 10: As can be seen in FIG. 13, a next step—enter adherence variables—another screen will be provided in which the physician selects whether the listed variables are present or not, or are unknown. In this example, all listed variables are selected as not being present in fields 132, 136-144 and 148-150, except for fields 134 and 146, which are selected as unknown.

Figure 14:
FIG. 14 is a screen shot illustrating an output report/analysis generated by an exemplary computer implemented method of the present invention.

Step 11: As can be seen in FIG. 14, a next step provides the output of the disease matrix algorithm to the physician based upon the previous inputs. As can be seen in this exemplary output, column 152 lists the recommended drugs for treating the patient, column 154 provides the score for each drug listed, column 156 provides a filed in which the physician can select to prescribe the drug, column 158 provides the recommended dosage for the patient, column 160 provides a bar-graph display for each drug listed that provides the five most relevant features in generating the score (the features are defined/explained in the box 161 to the right), and field 162 indicates the adherence percentage estimate for the patient. In this example, topiramate is recommended by the algorithm for the patient, having a score of 2850 and a recommended dosage of claim 100% of the listed dosage. The patient is calculated to have a 90% chance of adhering to the drug treatment.

CONCLUSION

Having described the invention with reference to the exemplary embodiments, it is to be understood that it is not intended that any limitations or elements describing the exemplary embodiment set forth herein are to be incorporated into the meanings of the patent claims unless such limitations or elements are explicitly listed in the claims. Likewise, it is to be understood that it is not necessary to meet any or all of the identified advantages or objects of the invention disclose herein in order to fall within the scope of any claims, since the invention is defined by the claims and since inherent and/or unforeseen advantages of the present invention may exist even though they may not be explicitly discussed herein.

Finally, it is to be understood that it is also within the scope of the invention to provide any computer, computer-system and/or computerized tool as is known by one of ordinary skill in the art that is designed, programmed or otherwise configured to perform any of the above-discussed methods, algorithms or processes.

All publications, patents, and patent applications mentioned in the specification are indicative of the level of those skilled in the art to which this invention pertains. All publications, patents, and patent applications are herein incorporated by reference to the same extent as if each individual publication or patent application was specifically and individually incorporated by reference.

What is claimed is:

1. A method for determining a starting dose of a neuropsychiatric drug for administration to a patient in need thereof, the method comprising:
    (a) receiving at a processor the usual drug dose for the population representing the patient (Dpop);
    (b) receiving at a processor the patient's genotype for a panel of genes comprising the following cytochrome P450 (CYP) genes: CYP2D6, CYP2C19, and CYP2C9;
    (c) determining the number of functional and non-functional alleles for each gene based on said genotype;
    (d) assigning the patient into a metabolizer phenotype subgroup based upon the number of functional alleles for each of the CYP genes wherein the metabolizer subgroup is selected from one of the following:
    Extensive metabolizer (EM)=2 functional alleles,
    Intermediate metabolizer (IM)=1 functional allele, and
    Poor metabolizer (PM)=0 functional alleles;
    (e) receiving at a processor the frequency of the metabolizer phenotype subgroups in the population;
    (f) determining, via a processor, the starting dose of the drug expressed as a percentage based on the number of non-functional alleles as follows:
    Percent reduction for one non-functional allele:
        (DREM %−DRIM %)/DREM %
    Percent reduction for two non-functional alleles:
        (DREM %−DRPM %)/DREM %
    wherein DRX % is the dosing recommendation for metabolizer subgroup X expressed as a percentage of the usual drug dose (Dpop),
    wherein DEM is reduced by 20% for every non-functional CYP2D6 or CYP2C19 allele and by 40% for every non-functional CYP2C9 allele, and
    (g) administering the starting dose of the drug determined in step (f) to the patient.

2. The method of claim 1, wherein the usual drug dose (Dpop) is reduced by
- 20% for every non-functional CYP2D6 allele detected in said patient and the drug is selected from the group consisting of atomoxetine, imipramine, perphenazine, doxepin, maprotiline, trimipramine, thioridazine, desipramine, clomipramine, zuclopenthixol, paroxetine, venlafaxine, flupentixol, and mianserin;
- 20% for every non-functional CYP2C19 allele detected in said patient and the drug is selected from the group consisting of trimipramine, amitryptiline, moclobemide, imipramine, citalopram, clomipramine, and fluoxetine; and
- 40% for every non-functional CYP2C9 allele detected in said patient and the drug is selected from the group consisting of glimepiride, glipizide, glyburide, losartan, hydrochlorothiazide, chlorpropamide, tolbutamide, tolazamide, and warfarin.

3. The method of claim 1 or 2, wherein the panel of genes in step (b) further comprises one or more genes selected from the group consisting of CYP1A2, CYP2E1, a serotonin transporter gene, a serotonin receptor gene, a dopamine transporter gene and a dopamine receptor gene.

4. The method of claim 3, wherein the alleles of for each gene are selected from the group consisting of CYP1A2*1A, CYP1A2*3, CYP2C19*1A, CYP2C19*1B, CYP2C19*2A, CYP2D6*1A, CYP2D6*2, CYP2D6*2N, CYP2D6*3, CYP2D6*4, CYP2D6*5, CYP2D6*6, CYP2D6*7, CYP2D6*8, CYP2D6*10, CYP2D6*12, or CYP2D6*17.

5. The method of claim 3, wherein said serotonin receptor gene encodes serotonin receptors 1A, 1B, 1D, 2A, or 2C.

6. The method of claim 3, wherein said dopamine receptor gene encodes dopamine receptors D1, D2, D3, D4, D5 or D6.

* * * * *

UNITED STATES PATENT AND TRADEMARK OFFICE
CERTIFICATE OF CORRECTION

| | | |
|---|---|---|
| PATENT NO. | : 8,589,175 B2 | Page 1 of 1 |
| APPLICATION NO. | : 12/085606 | |
| DATED | : November 19, 2013 | |
| INVENTOR(S) | : Glauser et al. | |

It is certified that error appears in the above-identified patent and that said Letters Patent is hereby corrected as shown below:

In the claims:

Claim 4, column 32, line 6, beginning sentence, "The method of claim 3, wherein the alleles of for each gene", should read: --The method of claim 3, wherein the alleles for each gene--

Signed and Sealed this
Twenty-eighth Day of January, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,589,175 B2 | Page 1 of 1 |
| APPLICATION NO. | : 12/085606 | |
| DATED | : November 19, 2013 | |
| INVENTOR(S) | : Glauser et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 772 days.

Signed and Sealed this
Twelfth Day of May, 2015

Michelle K. Lee
*Director of the United States Patent and Trademark Office*